US011980604B2

(12) United States Patent
Zeligs et al.

(10) Patent No.: US 11,980,604 B2
(45) Date of Patent: May 14, 2024

(54) METHODS FOR IMPROVED ENDOVASCULAR THROMBECTOMY USING 3,3'-DIINDOLYLMETHANE

(71) Applicant: Boulder BioScience LLC, Boulder, CO (US)

(72) Inventors: Michael A. Zeligs, Boulder, CO (US); Irwin C. Jacobs, Defiance, MO (US)

(73) Assignee: Boulder BioScience LLC, Boulder, CO (US)

( * ) Notice: Subject to any disclaimer, the term of this patent is extended or adjusted under 35 U.S.C. 154(b) by 0 days.

(21) Appl. No.: 18/054,111

(22) Filed: Nov. 9, 2022

(65) Prior Publication Data

US 2023/0104863 A1    Apr. 6, 2023

Related U.S. Application Data

(62) Division of application No. 17/303,353, filed on May 27, 2021, now Pat. No. 11,529,331.

(60) Provisional application No. 63/032,218, filed on May 29, 2020.

(51) Int. Cl.

| *A61K 31/404* | (2006.01) |
| *A61K 9/00* | (2006.01) |
| *A61K 31/122* | (2006.01) |
| *A61K 31/137* | (2006.01) |
| *A61K 31/203* | (2006.01) |
| *A61K 31/23* | (2006.01) |
| *A61K 31/4045* | (2006.01) |
| *A61K 31/41* | (2006.01) |
| *A61K 31/4427* | (2006.01) |
| *A61K 31/451* | (2006.01) |
| *A61K 31/4706* | (2006.01) |
| *A61K 31/51* | (2006.01) |
| *A61K 31/519* | (2006.01) |
| *A61K 31/5377* | (2006.01) |
| *A61K 31/704* | (2006.01) |
| *A61K 38/46* | (2006.01) |
| *A61K 38/48* | (2006.01) |
| *A61K 39/395* | (2006.01) |
| *A61P 7/02* | (2006.01) |
| *A61P 9/10* | (2006.01) |

(52) U.S. Cl.
CPC .......... *A61K 31/404* (2013.01); *A61K 9/0019* (2013.01); *A61K 9/0053* (2013.01); *A61K 31/122* (2013.01); *A61K 31/137* (2013.01); *A61K 31/203* (2013.01); *A61K 31/23* (2013.01); *A61K 31/4045* (2013.01); *A61K 31/41* (2013.01); *A61K 31/4427* (2013.01); *A61K 31/451* (2013.01); *A61K 31/4706* (2013.01); *A61K 31/51* (2013.01); *A61K 31/519* (2013.01); *A61K 31/5377* (2013.01); *A61K 31/704* (2013.01); *A61K 38/465* (2013.01); *A61K 38/482* (2013.01); *A61K 39/3955* (2013.01); *A61P 7/02* (2018.01); *A61P 9/10* (2018.01)

(58) Field of Classification Search
CPC .............. A61K 2300/00; A61K 31/122; A61K 31/137; A61K 31/203; A61K 31/225; A61K 31/23; A61K 31/404; A61K 31/4045; A61K 31/41; A61K 31/44; A61K 31/4427; A61K 31/451; A61K 31/4706; A61K 31/51; A61K 31/519; A61K 31/5377; A61K 31/704; A61K 38/2006; A61K 38/465; A61K 38/482; A61K 38/49; A61K 39/3955; A61K 45/06; A61K 47/02; A61K 47/10; A61K 47/14; A61K 47/22; A61K 47/24; A61K 47/44; A61K 9/0019; A61K 9/0053; A61K 9/1075; A61K 9/4858; A61K 9/4866; A61K 9/50; A61P 43/00; A61P 7/02; A61P 9/10
See application file for complete search history.

(56) References Cited

U.S. PATENT DOCUMENTS

| 7,348,352 B2 | 3/2008 | Zeligs |
| 7,989,486 B2 | 8/2011 | Zeligs |
| 8,080,577 B2 | 12/2011 | Zeligs |
| 8,236,848 B2 | 8/2012 | Zeligs |
| 8,552,052 B2 | 10/2013 | Zeligs |
| 9,918,965 B2 * | 3/2018 | Zeligs .................. A61K 31/122 |
| 10,441,569 B2 | 10/2019 | Zeligs et al. |
| 10,799,479 B2 | 10/2020 | Zeligs et al. |
| 2006/0100264 A1 | 5/2006 | Bjeldanes et al. |
| 2006/0111423 A1 | 5/2006 | Zeligs |
| 2006/0264497 A1 | 11/2006 | Zeligs |
| 2018/0280347 A1 | 10/2018 | Zeligs et al. |
| 2020/0138919 A1 | 5/2020 | Desilles et al. |
| 2021/0046046 A1 | 2/2021 | Zeligs et al. |

FOREIGN PATENT DOCUMENTS

| WO | 2015042170 A1 | 3/2015 |
| WO | 2020062780 A1 | 4/2020 |

OTHER PUBLICATIONS

Ali, Kolliphor® HS 15—An Enabler for Parenteral and Oral Formulations, Monday, Feb. 25, 2019 (Year: 2019).*
Wang, Molecules. Jun. 2019; 24(11): 2151. (Year: 2019).*
Sterile saline solution label, Nova-Tech Inc. Mar. 2020. (Year: 2020).*

(Continued)

*Primary Examiner* — Jean P Cornet

(74) *Attorney, Agent, or Firm* — Rimon, P.C.; Dale L. Rieger

(57) ABSTRACT

Provided herein are methods of enhancing mechanical thrombectomy during endovascular therapy for acute thrombosis using 3,3'-diindolylmethane.

5 Claims, 7 Drawing Sheets

(56) References Cited

OTHER PUBLICATIONS

Zhu et al. (United European Gastroenterol J. Jul. 2019; 7(6): 782-789), (Year: 2019).*
Fakhari et al. (Heliyon. Aug. 2017; 3(8): e00390). (Year: 2017).*
Kollikowski et al. "Local Leukocyte Invasion during Hyperactute Human Ischemic Stroke" Ann. Neurol. 2020, 87, 466-479.
Krams et al. "Acute Stroke Therapy by Inhibition of Neutrophils (ASTIN): An Adaptive Dose-Response Study of UK-279,276 in Acute Ischemic Stroke" Stroke 2003, 34, 2543-2548.
Li et al. "Intravenous antagomiR-494 lessens brain-infiltrating neutrophils by increasing HDAC2-mediated repression of multiple MMPs in experimental stroke" The FASEB J. 2020, 34, 6934-6949.
Mechtouff et al. "Association of Interleukin-6 Levels and Futile Reperfusion After Mechanical Thrombectomy" Neurology 2021, 96, e752-e757.
Novotny et al. "Thrombus NET content is associated with clinical outcome in stroke and myocardial infarction" Neurology 2020, 94, 1-e15.
Rockwell et al. "The effect of 3,3'-diindolylmethane (DIM) on plasma cytokine levels in healthy human subjects" Cancer Res. 2008, 68 (9 Supplement), 504.
Zhang et al. "Inflammatory markers as independent predictors for stroke outcomes" Brain Behavior 2021, 11, e01922.
Hamam et al., Biomolecules, May 11, 2019 ;9(5): 184 pp. 2-19 (Year: 2019).
Beaver et al., Toxicol Appl Pharmacol. Sep. 15, 2012; 263(3): 345-351 (Year: 2012).
Juana Valles et al., Thromb Haemost. Oct. 5, 2017;117(10): 1919-1929 (Year: 2017).
Cai et al., J Neuroinflammation Aug. 31, 2019; 16(1 ): 175. (Year: 2019).
Zhou etal., EBiomedicine, vol. 53, Mar. 2020, 102671, pp. 1-15 (Year: 2020).
Fischer et al., Stroke. 2017; 48:2912-2918. (Year: 2018).
Powers WJ, et al., Guidelines for the Early Management of Patients With Acute Ischemic Stroke: 2019 Update to the 2018 Guidelines for the Early Management of Acute Ischemic Stroke: A Guideline for Healthcare Professionals From the American Heart Association/American Stroke Association, Stroke, Dec. 2019;50(12):e344-e418.
Phan K et al., Endovascular Thrombectomy Alone versus Combined with Intravenous Thrombolysis, World Neurosurg., Dec. 2017; 108:850-858.
Fuchs T, et al. Extracellular DNA traps promote thrombosis, Proc Natl Acad Sci U S A, Sep. 7, 2010;107(36):15880-5.
Ducroux C et al. Thrombus Neutrophil Extracellular Traps Content Impair tPA-Induced Thrombolysis in Acute Ischemic Stroke, Stroke, Mar. 2018;49(3):754-757.
Boeckh-Behrens T et al. The Impact of Histological Clot Composition in Embolic Stroke, Clin Neuroradiol., Jun. 2016;26(2):189-97.
Peña-Martinez C, et al. Pharmacological Modulation of Neutrophil Extracellular Traps Reverses Thrombotic Stroke tPA (Tissue-Type Plasminogen Activator) Resistance, Stroke, Nov. 2019;50(11):3228-3237.
Novotny J, et al. Thrombus NET content is associated with clinical outcome in stroke and myocardial infarction. Neurology. Jun. 2, 2020;94:1-e15; doi:10.1212/WNL.0000000000009532.
Albers GW, et al.: Thrombectomy for stroke at 6 to 16 hours with selection by perfusion imaging, N Engl J Med, 378: 708-718, 2018.
Anderton et al., Clin. Cancer Res. 10:5233-5241 (2004).
Bradlow et al. in vivo, 24:387-392 (2010).
Anderton et al. Drug Metab. Disp., 32:632-638 (2004).
Haslett C, et al. Modulation of multiple neutrophil functions by preparative methods or trace concentrations of bacterial lipopolysaccharide Am J Pathol. Apr. 1985; 119(1):101-10.
Young RL, et al. Neutrophil extracellular trap (NET)-mediated killing of Pseudomonas aeruginosa: evidence of acquired resistance within the CF airway, independent of CFTR. Plos One. 2011;6(9):e23637.

Zuo et al. JCI Insight Apr. 24, 2020;138999. doi: 10.1172/jci.insight. 138999.
Novotny J, et al. Histological comparison of arterial thrombi in mice and men and the influence of Cl-amidine on thrombus formation, PLOS One, Jan. 2, 2018;13(1):e0190728. doi: 10.1371.
Fay WP, et al. Vitronectin inhibits the thrombotic response to arterial injury in mice, Blood, 1999; 93(6):1825-30.
Doyle, K. et al. Distal Hypoxic stroke: A new mouse model of stroke with high throughput, low variability and a quantifiable functional deficit J Neurosci Methods. 2012, 207(1): 31-40.
Almeida, M., Magalhães, M., Veiga, F. et al. Poloxamers, poloxamines and polymeric micelles: Definition, structure and therapeutic applications in cancer. J Polym Res 25, 31 (2018).
Wang X, et al. An optimized murine model of ferric chloride-induced arterial thrombosis for thrombosis research. Thromb Res. 2005;115(1-2):95-100.
Gunning GM, et al. Clot friction variation with fibrin content; implications for resistance to thrombectomy. J Neurointerv. Surg. 2017, 0:1-5.
Sporns PB. Ischemic Stroke: Histological Thrombus Composition and Pre-Interventional CT Attenuation Are Associated with Intervention Time and Rate of Secondary Embolism. Cerebrovasc Dis. 2017;44(5-6):344-350.
Uhl B, et al. Tissue plasminogen activator promotes postischemic neutrophil recruitment via its proteolytic and honproteolytic properties. Arterioscler Thromb Vasc Biol. Jul. 2014;34(7):1495-504.
El Amki M, et al. Neutrophils Obstructing Brain Capillaries Are a Major Cause of No-Reflow in Ischemic Stroke. Cell Rep. Oct. 13, 2020;33(2):108260.
Karatas H, et al. Thrombotic distal middle cerebral artery occlusion produced by topical FeCl(3) application: a novel model suitable for intravital microscopy and thrombolysis studies. J Cereb Blood Flow Metab 2011;31:1452-1460.
Hernandez-Jimenez M et al. Test repositioning for functional assessment of neurological outcome after experimental stroke in mice. PLOS One. 2017;12:e0176770.
Jolugbo P, et al. Thrombus Composition and Efficacy of Thrombolysis and Thrombectomy in Acute Ischemic Stroke. Stroke Mar. 2021;52(3):1131-1142.
Yuki I, et al. The impact of thromboemboli histology on the performance of a mechanical thrombectomy device. AJNR Am J Neuroradiol. Apr. 2012;33(4):643-8.
Hossmann KA The two pathophysiologies of focal brain ischemia: implications for translational stroke research. J Cereb Blood Flow Metab. Jul. 2012;32(7):1310-6.
Matsumoto, et al., J. Neuroimmunology, 2020, 342, 577195.
Paliwal, et al., Naunyn-Schmiedeberg's Archives of Pharmacology, 2018, 391, 613-625.
Park, et al., Phytotherapy Res., 2008, 22, 58-64.
Kasis et al. "Class IIa Histone Deacetylases Affect Neuronal Remodeling and Functional Outcome after Stroke" Neurochem Int. 2016, 96, 24-31.
Li et al. "Chemopreventive Agent 3,3'-Diindolylmethane Selectively Induces Proteasomal Degradation of Class I Histone Deacetylases" Cancer Res. 2010, 70(2), 646-654.
Offner et al. "Experimental stroke induces massive, rapid activation of the peripheral immune system" J. Cerebral Blood Flow & Metab. 2006, 26, 654-665.
Shoyaib et al. "Abstract TP114: Histone Deacetylase Inhibitors Panobinostat and Entinostat for Motor Recovery After Ischemic Stroke in Mice" International Stroke Conference 2020 Poster Abstracts Session Title: Basic and Preclinical Neuroscience of Stroke Recovery Posters II, Feb. 12, 2020, Stroke 2020, 51, ATP114.
Zhao et al. "Silencing of microRNA-494 inhibits the neurotoxic Th1 shift via regulating HDAC2-STAT4 cascade in ischaemic stroke" Br.J. Pharm., vol. 177, p. 128-144, first published Aug. 29, 2019.
McBride et al., Transl Stroke Res. 10.1007/s12975-017-0554-2, published online 2017 (Year: 2017).
Allen et al. "Sequence-specific MR Imaging Findings that are Useful in Dating Ischemic Stroke" RadioGraphics 2012, 32, 1285-1297.
Beleodaq (belinostat) for injection, for intravenous administration, Package Insert, Revised Jul. 2014.

(56) References Cited

OTHER PUBLICATIONS

Bui et al. "A Possible Association of Diindolylmethane with Pulmonary Embolism and Deep Venous Thrombosis" Case Reports in Medicine 2016, Article ID 7527098.

DeAngelo et al. "Phase Ia/II, two-arm, open-label, dose-escalation study of oral panobinostat administered via two dosing schedules in patients with advanced hamatologic malignancies" Leukemia 2013, 27, 1628-1636.

DeAngelo et al. "Phase Ia/II, two-arm, open-label, dose-escalation study of oral panobinostat administered via two dosing schedules in patients with advanced hamatologic malignancies" Leukemia 2013, 27, 1628-1636, Supplemental Methods.

Doyle et al. "Distal Hypoxic stroke: A new mouse model of stroke with high throughput, low variability and a quantifiable functional deficit" J. Neurosci. Methods 2012, 207(1), 31-40.

Farydak (panobinostat) capsules, for oral use, Package Insert, Revised Feb. 2015.

Hamam et al. "Histone Acetylation Promotes Neutrophil Extracellular Trap Formation" Biomolecules 2019, 9, 32.

Hernandez-Jimenez et al. "Test repositioning for functional assessment of neurological outcome after experimental stroke in mice" PLOS One 2017, doi.org/10.1371/journal.pone.0176770.

Hossmann "The two pathophysiologies of focal brain ischemia: implications for translational stroke research" J. Cerebral Blood Flow & Metab. 2012, 32, 1310-1316.

Karatas et al. "Thrombotic distal middle cerebral artery occlusion produced by topical FeCl3 application: a novel model suitable for intravital microscopy and thrombolysis studies" J. Cerebral Blood Flow & Metab. 2011, 31, 1452-1460.

Kim et al. "Deregulation of HDAC1 by p25/Cdk5 in Neurotoxicity" Neuron 2008, 60, 803-817.

Kim et al. "Neutrophil extracellular trap induced by HMGB1 exacerbates damages in the ischemic brain" Acta Neuropath. Commun. 2019, 7, 94.

Perez, et al. Pharm. Technol. Hosp. Pharm., 2016, 1(2), 91-103.

Danaei, et al. Pharmaceutics, 2018, 10, 57.

* cited by examiner

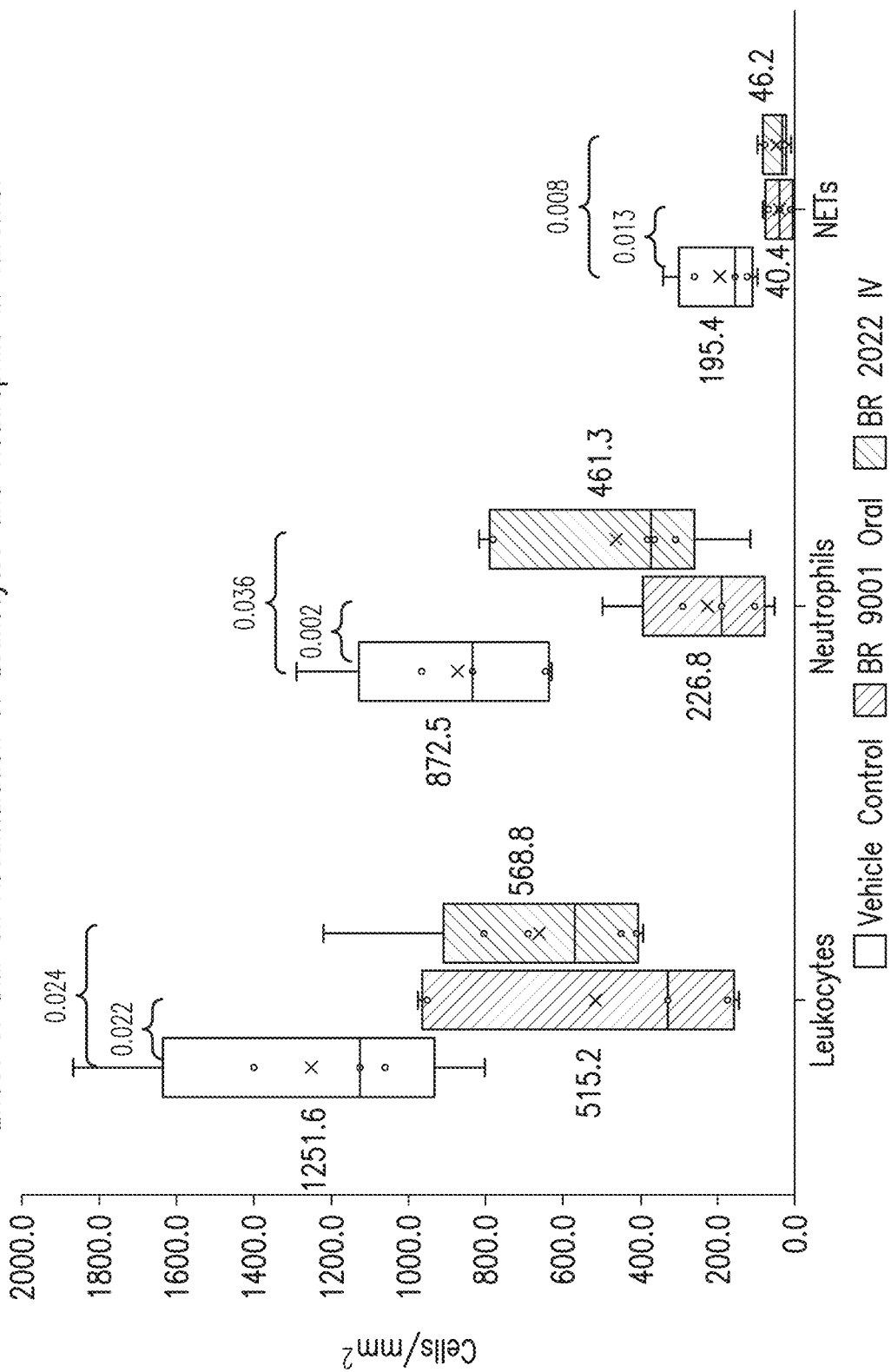

METHODS FOR IMPROVED ENDOVASCULAR THROMBECTOMY USING 3,3'-DIINDOLYLMETHANE

RELATED APPLICATIONS

This application is a divisional application under 35 U.S.C. §§ 120 and 121 of U.S. application Ser. No. 17/303,353, filed May 27, 2021, which claims priority to U.S. Provisional Application No. 63/032,218, filed May 29, 2020. The contents of the above-referenced applications are incorporated by reference herein in their entirety.

FIELD

Provided herein are methods and compositions utilizing 3,3'-diindolylmethane to enhance mechanical thrombectomy during endovascular therapy for acute thrombosis.

BACKGROUND

Thrombotic stroke is a leading cause of acute brain injury, death, and disability worldwide with increasing incidence as populations age. In the US, 87% of all strokes are Acute Ischemic Strokes (AIS). These account for about 690,000 AIS per year according to the Center for Disease Control and Prevention. Updates to the AIS guidelines released in 2019 now include endovascular therapy (EVT) using direct mechanical thrombectomy (MT) as a recommended intervention in addition to thrombolytic therapy with Tissue Plasminogen Activator (tPA) drugs. MT, as part of EVT using angiographically directed guidewires, catheters, and stent retrievers, is now credited with faster and more complete brain reperfusion for many patients. EVT of large vessel occluding thromboses (LVO) is now a standard of care and considered a mainstay of stroke treatment (Powers W J, et al., Guidelines for the Early Management of Patients With Acute Ischemic Stroke: 2019 Update to the 2018 Guidelines for the Early Management of Acute Ischemic Stroke: A Guideline for Healthcare Professionals From the American Heart Association/American Stroke Association, Stroke, 2019 December; 50(12):e344-e418). However, AIS patients treated with tPA and MT or MT alone still have uncertain outcomes that relate to resistance to tPA activity for lysing LVO thromboses, complete or partial failure of the MT procedure, and poor long-term outcome despite MT. In a meta-analysis of multiple studies, a lack of difference in outcome between MT alone and tPA plus MT treated patients in the setting of similar LVO showed that tPA is ineffective and insufficient as an adjunctive therapy for MT (Phan K et al., Endovascular Thrombectomy Alone versus Combined with Intravenous Thrombolysis, World Neurosurg., 2017 December; 108:850-858.e2.) Thus, a need for more effective adjunctive medical therapy for MT exists.

Histologic evaluation of thrombi removed from patients during MT and clinical correlation has revealed that a higher percentage of white blood cells (WBCs) in the thrombus is associated with a greater number of device passes, an extended MT time, and less favorable recanalization. Neutrophils (PMNs) are a predominant WBC type present in thrombi as well as Neutrophil Extracellular Traps (NETs). Prior studies have demonstrated the role of PMNs and NETs in thrombus formation (Fuchs T, et al. Extracellular DNA traps promote thrombosis, Proc Natl Acad Sci USA, 2010 Sep. 7; 107(36):15880-5). NETs are web-like structures of DNA and proteins expelled from activated PMNs that ensnare pathogens as part of the innate or non-specific immune response. In the non-infectious setting of AIS, NET formation can lead to thrombus formation and clot propagation through NET interaction with platelets and atheromatous blood vessel walls. In forming NETs, PMNs execute a programmed process by which plasma membrane pores are formed, coiled nuclear proteins and DNA are uncoiled, and the nuclear contents are forcibly extruded into the extracellular space.

NET formation and propagation triggers subsequent formation of a growing thrombus and downstream release of microthrombi which occlude small blood vessels, limiting blood flow and oxygen delivery to brain tissue in the case of AIS. This self-perpetuating immunopathologic process causes progressive damage to the brain, and analogous damage to the heart during myocardial infarction. Key enzymes in the formation of NETs are: neutrophil elastase (NE), which degrades intracellular proteins and triggers nuclear disintegration; peptidyl arginine deiminase type 4 (PAD4), which converts histones to citrullinates that facilitates the decondensation and release of the chromosomal DNA; and gasdermin D, which generates pores in the membrane of the neutrophil, thereby facilitating cell membrane rupture and the expulsion of DNA and the associated proitein molecules. Excessive NET formation can trigger a cascade of inflammatory reactions that triggers thrombosis, obstructs arterial blood flow, and results in hypoxic organ damage. Currently, there is no known effective therapy to inhibit or control NET production and propagation by activated PMNs. The problem of microthrombosis triggered by NET formation in small blood vessels is a distinct process from thrombus formation due to tissue factor activation of platelets or due to fibrin deposition secondary to activation of the intrinsic clotting cascade. Therefore, current approaches using anti-platelet therapeutics and anti-thrombotic drugs like tPA which digests only fibrin clots do not solve the problem of NETosis. NETosis describes a condition of proliferating NETs within an organ or thrombus, which predisposes to the attraction of additional PMNs, further NET formation and progressive thrombus propagation. Thrombi with a higher percentage of leukocytes or NETs were associated with an extended mechanical recanalization time, number of device passes, and less favorable recanalization (Ducroux C et al. Thrombus Neutrophil Extracellular Traps Content Impair tPA-Induced Thrombolysis in Acute Ischemic Stroke, Stroke, 2018 March; 49(3):754-757). The amount of leukocytes and NETs may be associated with the thrombus age and degree of thrombus organization. As the thrombus is organized, the strength of adherence to the vessel wall may increase, making the removal or aspiration of thrombus more difficult (Boeckh-Behrens T et al. The Impact of Histological Clot Composition in Embolic Stroke, Clin Neuroradiol., 2016 June; 26(2): 189-97).

Due to a poor understanding of the activation mechanisms of NET formation and unwanted activity to trigger thrombosis, there are only a limited number of drugs in development to control NET activity. These include development of inhibitors against the NE enzyme. Current Phase I investigation of NE inhibitors include lonodelestat (POL6014), alvelestat, CHF6333, and elafin. Colchicine is an existing drug that may inhibit neutrophil recruitment to sites of inflammation and the secretion of IL1β, a cytokine which promotes NET production. IL1β, Interleukin 8 (IL-8), and Interleukin 6 (IL-6) are inflammatory cytokines, which may promote NET production in AIS and other thrombotic conditions. A recombinant DNase I (dornase alfa), delivered by inhalation, is approved to dissolve NETs in the airways of patients with Cystic Fibrosis to clear mucus and improve symptoms. Dornase alfa does not influence NET production from PMNs. Dornase alfa is normally administered through nebulizers limiting its usefulness in treating NETosis associated with intravascular thrombosis. While DNAase enzyme therapy has limited use to partially dissolve NET-related thrombi after they are formed, DNAase therapy does nothing to inhibit the generation of NETs from activated PMNs.

NETs are associated with AIS and LVO and numbers of NETs correlate with the severity of brain injury and post stroke neurologic deficit in animal models of AIS (Peña-Martinez C, et al. Pharmacological Modulation of Neutrophil Extracellular Traps Reverses Thrombotic Stroke tPA (Tissue-Type Plasminogen Activator) Resistance, Stroke, 2019 November; 50(11):3228-3237). NETs are increased in LVO AIS and accumulate with increased time past stroke occurrence. In addition, with high NET thrombosis count, NETS are associated with the difficulty of performing MT, associated with failed thrombectomy, the need for more instrument passes to remove clot, and with poor outcome in both AIS and acute myocardial infarction (AMI) (Novotny J, et al., Thrombus NET content is associated with clinical outcome in stroke and myocardial infarction, Neurology, 2020 May 20:10). Even with the advances of EVT and MT, there is a lack of an available medicinal agent that facilitates successful MT and improves successful outcomes for MT. The absence of a small molecule drug to inhibit NET formation, acting within PMNs to arrest activation and limit progression to NET propagation represents an important unmet medical need. There is an immediate therapeutic need for an anti-NET small molecule drug to limit NET formation, limit subsequent thrombus formation, and reduce adherence to blood vessel walls. Following AIS, NETs are associated with resistance to tPA therapeutic response. Currently, response to EVT using MT for LVO only returns about 50% of patients to full function at 90 days post stroke when thrombectomy is successful (Albers G W, et al.: Thrombectomy for stroke at 6 to 16 hours with selection by perfusion imaging, N Engl J Med, 378: 708-718, 2018). A need exists to control NET formation in the setting of AIS adding a new modality to adjunctive medical treatment of MT in order to improve AIS treatment success rate and long-term outcome.

Currently there is no available drug that reduces NET formation and NET propagation applicable to the clinical setting of EVT and MT. Such a therapeutic compound would provide an important advance in the medical management of thrombosis before, during, and following EVT.

SUMMARY

Provided herein are methods of treating a subject undergoing EVT with MT for LVO by administering to the subject having a thrombosis a therapeutically effective amount of 3,3'-diindolylmethane (DIM) or a DIM analog. In one embodiment, DIM or a DIM analog is administered to the subject in a self-microemulsifying drug delivery system ("SMEDDS") formulation. In another embodiment, DIM or a DIM analog is administered intravenously as a microparticle suspension. In an additional embodiment, DIM is administered as part of combination therapy with another NET inhibitory agent, such as recombinant DNase I, anti-IL1β and/or Interleukin 8 (IL-8) monoclonal antibodies. In another embodiment, DIM or a DIM analog is administered in combination or alternation with another agent that ameliorates one or more aspects of EVT for MT of thrombosis including intravenous or intra-arterial recombinant tissue plasminogen activator (tPA)(e.g., Activase® (alteplase)). In certain embodiments, the subject has suffered an AIS or an acute myocardial infarction (AMI). In further embodiments, the AIS involves the anterior or posterior cerebral arteries and is subject to MT according to current stroke management guidelines (Powers W J, et al., Guidelines for the Early Management of Patients With Acute Ischemic Stroke: 2019 Update to the 2018 Guidelines for the Early Management of Acute Ischemic Stroke: A Guideline for Healthcare Professionals From the American Heart Association/American Stroke Association, Stroke, 2019 December; 50(12):e344-e418.).

Without being bound by any theory, it has been shown herein that DIM is effective in inhibiting NET formation and propagation from activated polymorphonuclear neutrophils (PMNs), and thus provides a new small molecule therapeutic active pharmaceutical ingredient (API) to control NET-related thrombosis propagation, resistance to MT, and reduce organ damage associated with NETs and an uncontrolled NETotic immunothrombotic response. As described in Novotny J, et al. (supra), NETs appear to be a key contributor to extended mechanical recanalization time during MT, a cause of increased number of device passes during MT, a cause of less favorable recanalization success rates following MT, and a contributor to the strength of adherence of thrombus to blood vessel walls which increases the difficulty of removal or aspiration of thrombus during EVT. Therefore, DIM or a DIM analog should have a positive effect in patients undergoing EVT with MT, in particular patients with AIS and LVO undergoing MT.

BRIEF DESCRIPTION OF THE DRAWINGS

FIGS. 1A and 1B show the time course of DNA release detected by Sytox Orange (representative of 2 independent experiments) as a proportion of DNA released compared to total release in the presence of saponin. 30veh=30 µM "equivalent" amount of SMEDDS excipients. FIGS. 1C and 1D show the time course of DNA release detected by MNase assay (at 4 h; n=3). Studies were conducted in the presence of F Protein (1 µg/mL) and SMEDDS DIM (1, 3, 10 and 30 µM)(FIGS. 1A and 1C); or LPS (10 µg/mL) and SMEDDS DIM (30 µM)(FIGS. 1B and 1D).

FIG. 3A shows representative time course of DNA release detected by Sytox Orange in the presence of F Protein (F; 1 µg/ml) and free DIM at 1, 3, 10, and 30 µM. FIG. 3B shows composite results of 7 independent Sytox Orange experiments depicted in FIG. 3A (mean+SEM) at 4 hrs. *P<0.05; **P<0.01 vs F Protein alone. NS, non-stimulated controls. FIG. 3C shows visualization of neutrophil DNA released in the presence of F Protein or LPS (10 µg/ml) in the presence and absence of free DIM.

FIG. 7 shows quantitative cell counting results in a composite summary chart of Immunofluorescent (IF) antibody identified Leukocytes (CD45), Neutrophils (LyG6), and NETs (CitH3). Results presented include group mean cell counts, ranges of cell counting results for each cell type, and comparison brackets indicating p values and levels of statistically significant differences between Vehicle Control (Group 1) and the two DIM treatment groups, Group 2 (BR9001 Oral), and Group 3 (BR2022 IV).

DETAILED DESCRIPTION

I. Definitions

Figure 1A:
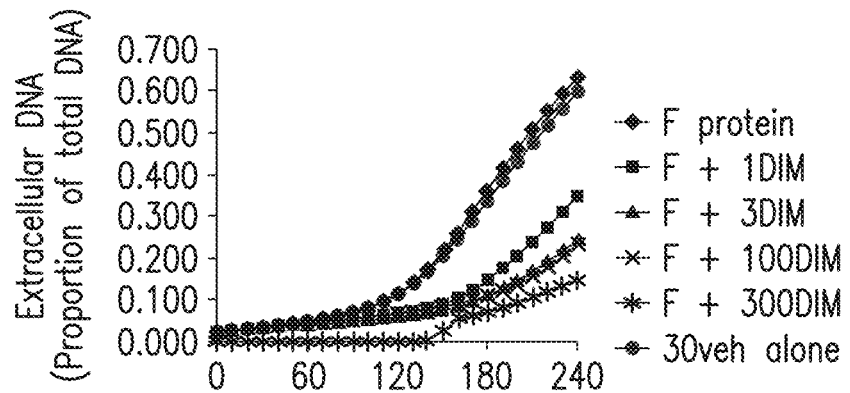
FIGS. 1A-1D show extracellular DNA release in the presence of F Protein and DIM in a SMEDDS formulation (i.e., BR-9001, Example 1).

To facilitate understanding of the disclosure set forth herein, a number of terms are defined below.

Unless defined otherwise, all technical and scientific terms used herein have the same meaning as is commonly understood by one of ordinary skill in the art. All patents, applications, published applications and other publications are incorporated by reference in their entirety. In the event that there are a plurality of definitions for a term herein, those in this section prevail unless stated otherwise.

The singular forms "a," "an," and "the" include plural references, unless the context clearly dictates otherwise.

As used herein "subject" is an animal, such as a mammal, including human, such as a patient.

As used herein, biological activity refers to the in vivo activities of a compound or physiological responses that result upon in vivo administration of a compound, composition or other mixture. Biological activity, thus, encompasses therapeutic effects and pharmacokinetic behavior of such compounds, compositions and mixtures. Biological activities can be observed in in vitro systems designed to test for such activities.

As used herein, DIM refers to 3,3'-diindolylmethane.

As used herein, a "DIM analog" refers to 1,1-bis(3,3'-indolyl)ethane ("HB-237"), 2-(indol-3-ylmethyl)-3,3'-diindolylmethane ("LTR") and/or indole-3-carbinol (1H-indolylmethanol).

As used herein, a "SMEDDS DIM" formulation refers to a self-microemulsifying drug delivery system containing DIM or a DIM analog. In one embodiment, a SMEDDS DIM formulation is a pharmaceutical composition of lipid-based excipient(s) in which DIM or a DIM analog is dissolved, providing a highly bioavailable, oral formulation.

As used herein, neutrophils are a type of immune cell that have granules (small particles) with enzymes that are released during infections. Activated neutrophils are the source of NETs.

As used herein, neutrophil extracellular traps ("NETs") are web-like structures of DNA and proteins expelled from activated polymorphonuclear neutrophils ("PMNs") that are intended to ensnare pathogens as part of the innate or non-specific immune response.

As used herein, NETosis is a unique form of cell programmed death that is characterized by the release of decondensed chromatin and granular contents to the extracellular space.

As used herein, LVO is an abbreviation for Large Vessel Occlusion which refers to a thrombus blocking blood flow through cerebral arteries, including anterior, middle, and posterior cerebral arteries.

As used herein, microthrombosis is a microscopic thrombus (blood clot) associated with and triggered by NETs.

As used herein, EVT is an abbreviation for Endovascular Therapy which refers to gaining percutaneous or surgical access to arteries or veins and using catheter-based techniques to perform transluminal thrombectomy, stent placement and balloon angioplasty.

As used herein, MT is an abbreviation for Mechanical Thrombectomy which includes all aspects of the interventional radiologic procedure of removal of occluding thromboses from obstructed arteries and veins.

As used herein, AIS is an abbreviation for Acute Ischemic Stroke.

As used herein, Acute Myocardial Infarction (AMI) is a well-recognized medical condition associated with atheromatous plaque rupture, thrombus formation, occlusion of a coronary artery, changes in the electrocardiogram (EKG), and symptoms of chest and left arm pain associated with clinical laboratory evidence of myocardial damage.

As used herein, Acute Coronary Syndrome (ACS) is a well-recognized medical term for a group of conditions that suddenly stop or severely reduce blood from flowing to the heart muscle. When blood cannot flow to the heart muscle, the heart muscle can become damaged. AMI and unstable angina are both acute coronary syndromes (ACS).

As used herein, EMT is an abbreviation for Emergency Medical Technician and is a person who is specially trained and certified to give emergency medical care including oral and intravenous medicines to patients before they reach a healthcare facility or during inter-facility transport.

As used herein, treatment means any manner in which one or more of the symptoms of a disease or disorder are ameliorated or otherwise beneficially altered. Treatment also encompasses any pharmaceutical use of the compositions herein, such as use for treating intravascular thrombosis, including endovascular therapy (EVT) using mechanical thrombectomy (ME) for acute ischemic stroke (AIS) and or myocardial infarction (MI).

As used herein, amelioration of the symptoms of a particular disorder by administration of a particular compound or pharmaceutical composition refers to any lessening, whether permanent or temporary, lasting or transient that can be attributed to or associated with administration of the compound or pharmaceutical composition. Amelioration of the symptoms of a particular disorder also includes lessening the duration of illness and/or speeding the time of recovery from illness attributed to the particular disorder.

As used herein, and unless otherwise indicated, the terms "manage," "managing" and "management" encompass preventing the recurrence of the specified disease or disorder in a subject who has already suffered from the disease or disorder. The terms encompass modulating the threshold, development and/or duration of the disease or disorder, or changing the way that a subject responds to the disease or disorder.

As used herein, the $IC_{50}$ refers to an amount, concentration or dosage of a particular test compound that achieves a 50% inhibition of a maximal response in an assay that measures such response.

II. Methods of Treatment

Provided herein are methods of treating a subject having AIS or AMI and undergoing MT by administering to the subject an effective amount of DIM or a DIM analog. In one embodiment, provided herein is a method of treating a subject having AIS for whom treatment with tPA is contraindicated by administering DIM or a DIM analog to the subject. In another embodiment, provided herein is a method of preventing or limiting resistance to tPA activity in a subject with AIS by co-administering DIM or a DIM analog in addition to tPA to the subject. In another embodiment, provided herein is a method of treating a subject having AIS and undergoing EVT and MT by administering DIM or a DIM analog to the subject. In another embodiment, provided herein is a method of treating an AIS candidate for EVT with imaging indicating a large anterior cerebral circulation occlusion from 1 to 16 or more hours from when last seen healthy by administering DIM or a DIM analog to the subject.

In another embodiment, provided herein is a method of treating a subject having AMI by administering DIM or a DIM analog to the subject before, during or immediately after MT performed as part of a percutaneous transluminal coronary angioplasty (PTCA) procedure.

Also provided are methods of inhibiting NET formation and propagation from PMNs by contacting the PMNs with DIM or a DIM analog.

In certain embodiments, DIM or a DIM analog is formulated in a SMEDDS formulation for oral administration. In other embodiments, DIM or a DIM analog is formulated for intravenous administration.

The addition of an early, pre-EVT dose of DIM or a DIM analog in a SMEDDS formulation or intravenous DIM or DIM analog is a protocol-ready addition to existing AIS emergency management protocols, which will not interrupt the time-sensitive progress of patients into the hands of interventional radiologists for EVT and MT. Adding a complementary drug product like oral or intravenous DIM or a DIM analog to tPa in the clinical trial setting is expected to improve outcomes of the use of tPA alone and following high risk EVT with MT. Using the EVT pool of cases will allow accrual of cohorts of patients with similar anterior circulation stroke anatomy for comparison of outcomes in placebo-controlled Phase I and II studies. Short-term oral use of DIM in a SMEDDS formulation (e.g., BR-9001) in clinical trials for no more than one week in an AIS patient is supported by the duration of a completed 28 day GLP safety study of BR-9001 in rodents (McCormick D L, et al., 28-Day Toxicology and Toxicokinetics Study of BR-9001 in Rats, DCP HHSN26100003, 2019). This safety data supports IND filing once a successful animal efficacy study showing benefit of DIM in a model of AIS is performed. Both patient family members and physicians will be highly motivated to enroll AIS patients in clinical trials using BR-9001 due to the need to further improve outcomes in AIS patients.

Improving outcomes for EVT associated MT for AIS by using DIM in a SMEDDS formulation (e.g., BR-9001) in association with tPA (e.g., Activase® (alteplase)) or EVT alone without tPA addresses a major unmet need for an agent to mitigate both thrombosis propagation and ischemia reperfusion injury in brain. No approved drug product exists for this open indication. The use of DIM in a SMEDDS formulation (e.g., BR-9001) in combination with EVT and MT has potential for early adoption by interventional radiologists and rapid expanded use for management of additional thromboses at various anatomic sites. The use of DIM in a SMEDDS formulation (e.g., BR-9001) or intravenously (e.g., BR2022 IV (Example 4) or Formulation #8 (Example 11)) in combination with tPA is also contemplated when EVT is not available to inhibit the neutrophil activating activity of tPA used as a single agent. Combined administration of DIM with tPA in the absence of EVT or in the setting of failed MT is indicated to inhibit neutrophil activation and NETosis which contributes to the clinical occurrence of tPA resistance (Ducroux C, et al., 2018, supra).

In certain embodiments, the methods provided herein exhibit one or more of the following improvements over existing therapy by using DIM in MT for AIS and by using DIM with tPA for AIS without MT:

1. Improve the success rate for clot retrieval and restoration of cerebral circulation associated with MT for AIS;
2. Improve the functional outcome of stroke patients who undergo EVT using MT;
3. Improve the outcome of adjunctive medical therapy with includes tPA, DNase, PAD4 inhibitors, Complement inhibitors, Von Willebrand Factor (VWF) inhibitors, monoclonal antibodies etc.;
4. Expand the time window associated with successful MT for AIS;
5. Advance the pre-hospital medical management of AIS with an orally administered agent;
6. Provide an IV agent for intra procedure and inter-hospital intervention to improve the success and outcome of AIS treatment;
7. Increase the proportion of AIS patients with LVO qualifying by guidelines as candidates for MT who qualify for conscious sedation versus general anesthesia; and/or
8. Decrease the interval between occurrence of stroke time and interventional radiologyto "needle time" in management of LVO with MT.

The dosage and administration of pharmaceutical compositions of DIM or a DIM analog in the clinical setting of AIS includes oral DIM compositions for conscious patients and intravenous DIM compositions for stuporous or sedated patients. For conscious patients with symptoms of AIS, oral administration should be as soon as possible after AIS and before EVT. In one embodiment, the composition and dosage is a SMEDDS DIM formulation providing 200-500 mg DIM per oral administration, repeated after 4-8 hours three times and thereafter every 12 hours for 3-5 days. For AIS patients who are stuporous or sedated, intravenous (IV) administration of DIM is from a micro-suspension of DIM (e.g., Examples 4 and 11). In one embodiment, the dosage of IV DIM is from 50-200 mg DIM administered with a 30-minute infusion, repeated after 4-8 hours three times and thereafter every 12 hours for up to 3-5 days. In other embodiments, oral and IV compositions of DIM are administered when used in conjunction with tPA (Activase (alteplase)) or related Tenecteplase (TNKASE®). In addition, oral and IV compositions of DIM are used in the clinical settings of AIS, ACS, and AMI without tPA when some of the contraindications to the use of tPA exist.

III. Combination Therapy with a Second Active Agent

The methods provided herein utilizing DIM or a DIM analog can also be combined or used in combination with other therapeutic agents useful in the inhibition of PMN activation, NET formation, and NET propagation before, during, and after intravascular thrombosis.

In one embodiment, provided herein is a method of treating, preventing, or managing AIS or AMI, comprising administering to a subject DIM or a DIM analog in combination with one or more second active agents.

As used herein, the term "in combination" includes the use of more than one therapy (e.g., one or more prophylactic and/or therapeutic agents). However, the use of the term "in combination" does not restrict the order in which therapies (e.g., prophylactic and/or therapeutic agents) are administered to a subject with a disease or disorder. A first therapy (e.g., a prophylactic or therapeutic agent such as a compound provided herein, a compound provided herein, e.g., the compound provided herein, or a derivative thereof) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to the subject. Triple therapy is also contemplated herein.

Administration of DIM or a DIM analog and one or more second active agents to a subject can occur simultaneously or sequentially by the same or different routes of administration. The suitability of a particular route of administration employed for a particular active agent will depend on the active agent itself (e.g., whether it can be administered orally without decomposing prior to entering the blood stream) and the disease or disorder being treated.

The route of administration of DIM or a DIM analog is independent of the route of administration of a second therapy. In one embodiment, DIM or a DIM analog is administered orally. In another embodiment, DIM or a DIM analog is administered intravenously. Thus, in accordance with these embodiments, DIM or a DIM analog is administered orally or intravenously, and the second therapy can be administered orally, parenterally, intraperitoneally, intravenously such as with intravenous tPA, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form. In one embodiment, DIM or a DIM analog and a second therapy are administered by the same mode of administration, orally or by IV. In another embodiment, DIM or a DIM analog is administered by one mode of administration, e.g., by IV, whereas the second agent is administered by another mode of administration, e.g., orally.

In one embodiment, the second active agent is administered intravenously, such as with tPA, or subcutaneously and once or twice daily in an amount of from about 1 to about 1000 mg, from about 5 to about 500 mg, from about 10 to about 350 mg, or from about 50 to about 200 mg. The specific amount of the second active agent will depend on the specific agent used, the severity and stage of disease being treated, and the amount of DIM or a DIM analog and any optional additional active agents concurrently administered to the subject.

One or more second active ingredients or agents can be used together with DIM or a DIM analog in the methods and compositions provided herein. Second active agents can be large molecules (e.g., proteins) or small molecules (e.g., synthetic inorganic, organometallic, or organic molecules).

In one embodiment, DIM or a DIM analog can be administered in an amount ranging from about 0.1 to about 900 mg, from about 25 to about 300 mg, or from about 25 to about 400 mg orally up to 3-4 times daily alone, or in combination with a second active agent, prior to, during, or after the use of conventional therapy.

In another embodiment, DIM or a DIM analog is delivered in a SMEDDS excipient formulation in liquid filled capsules containing from 25-100 mg DIM or a DIM analog per capsule taken orally or administered to the patient through a nasogastric tube.

In another embodiment, DIM or a DIM analog is delivered in a SMEDDS excipient formulation in liquid filled capsules which contain DIM or a DIM analog and a second active compound selected from vitamin B1, vitamin K2, Melatonin, Chloroquine, Ebselen, Retinyl Palmitate, and/or Tretinoin, or a combination thereof.

In another embodiment, DIM or a DIM analog is delivered in a SMEDDS excipient formulation in liquid filled capsules which contain DIM or a DIM analog and a second active compound selected from vitamin B1, vitamin K2, Melatonin, Chloroquine, Glycyrrhizin (Glycyrrhizic acid), Ebselen, Retinyl Palmitate, and/or Tretinoin, or a combination thereof.

In a further embodiment, DIM or a DIM analog is delivered in combination with a second active compound which include Complement Cascade inhibitors, Intrinsic or Extrinsic Coagulation Factor inhibitors, High mobility group box 1 protein (HMBP1) inhibitors, including Glycyrrhizic acid and Glycyrrhizin, or Von Willebrand Factor (VFW) inhibitors. Complement Cascade inhibitors include the small molecule drugs CCX168 (ChemoCentryx), ACH145951 (Achillion), and LPN023 (Novartis). Coagulation Factor inhibitors include Factor XII inhibitors, and Factor XIa inhibitors (EP-7041, and BAY 2433334).

Examples of second active agents for use in the compositions and methods provided herein include: Ionodelestat (POL6014), alvelestat, CHF6333, elafin, Anakinra, Canakinumab (ACZ885, Ilaris), Eptifibatide Injection, Butylphthalide, Tenecteplase, Activase (tPA), Dimethyl Fumarate (Tecfidera), Fingolimod (FTY720), Etanercept (TNF-inhibitor), HuMax-IL8 (BMS-986253), Natalizumab (Tysabri), Elezanumab (ABT-555), Ebselen, Optaplimistat (SP-8203), ADAMTS13, Chloroquine, Hydroxychloroquine, Glycyrrhizin (Glycyrrhizic acid), Tretinoin, Retinylpalimitate, N-α-benzoyl-N5-(2-chloro-1-iminoethyl)-1-ornithine amide (Cl-amidine, Calbiochem, #506282), Emapalumab, tocilizumab (RoActemra), sarilumab (Kevzara), Eptifibatide Injection, Butylphthalide, Ticagrelor (Brilinta), acalabrutinib, ibrutinib, rilzabrutinib, sarilumab, siltuximab, tocilizumab, baricitinib, ruxolitinib, CR2-Crry, B4Crry, Minocycline, NR58-3.14.3, Rinalocept, Gevokizumab and Optaplimistat (SP-8203).

In another embodiment, examples of second active agents for use in the compositions and methods provided herein include: lonodelestat (POL6014), alvelestat, CHF6333, elafin. Anakinra, Canakinumab (ACZ885, Ilaris), Eptifibatide Injection, Butylphthalide, Tenecteplase, Activase (tPA), Dimethyl Fumarate (Tecfidera), Fingolimod (FTY720), Etanercept (TNF-inhibitor), HuMax-IL8 (BMS-986253), Natalizumab (Tysabri), Elezanumab (ABT-555), Ebselen, Optaplimistat (SP-8203), ADAMTS13, Chloroquine, Hydroxychloroquine, Tretinoin, Retinylpalimitate, N-α-benzoyl-N5-(2-chloro-1-iminoethyl)-1-ornithine amide (Cl-amidine, Calbiochem, #506282), Emapalumab, tocilizumab (RoActemra), sarilumab (Kevzara), Eptifibatide Injection, Butylphthalide, Ticagrelor (Brilinta), acalabrutinib, ibrutinib, rilzabrutinib, sarilumab, siltuximab, tocilizumab, baricitinib, ruxolitinib, CR2-Crry, B4Crry, Minocycline, NR58-3.14.3, Rinalocept, Gevokizumab and Optaplimistat (SP-8203).

In certain embodiments, the second active agent is selected from those shown in the following table.

therapy for psoriasis (trade name Fumaderm). Since 2013, it has been approved by the U.S. Food and Drug Administration as a treatment option for adults with relapsing multiple sclerosis (trade name Tecfidera).

Anakinra (brand name Kineret) is a biopharmaceutical drug used to treat rheumatoid arthritis. It is a recombinant and slightly modified version of the human interleukin 1 receptor antagonist protein. It is marketed by Swedish Orphan Biovitrum.

Fingolimod (INN, trade name Gilenya, Novartis) is an immunomodulating drug, mostly used for treating multiple sclerosis (MS). Fingolimod is a sphingosine-1-phosphate receptor modulator, which sequesters lymphocytes in lymph nodes, preventing them from contributing to an autoimmune reaction.

Natalizumab, sold under the brand name Tysabri among others, is a medication used to treat multiple sclerosis and Crohn's disease. It is a humanized monoclonal antibody against the cell adhesion molecule α4-integrin. Previously, it has been given by intravenous infusion every 28 days.

Canakinumab (ACZ885, Ilaris) is a human anti-IL-1β monoclonal antibody developed by Novartis. Its mode of action is based on the neutralization of IL-1β signaling, resulting in suppression of inflammation in patients with disorders of autoimmune origin.

Tocilizumab, also known as atlizumab, Actemra/RoActemra (Roche) is an immunosuppressive drug, mainly for the treatment of rheumatoid arthritis (RA) and systemic juvenile idiopathic arthritis, a severe form of arthritis in children. It is a humanized monoclonal antibody against the interleukin-6 receptor (IL-6R). Interleukin 6 (IL-6) is a cytokine that plays an important role in immune response

| Drug (Other Name) (Manufacturer) | Class | Molecular or Cellular Target | Dosage (Route of Administration) | Molecular Weight and Log P |
|---|---|---|---|---|
| Dimethyl Fumarate (Tecfidera) (Biogen) | Immune Modulator | 1-glutathione (GSH) and ROS modulation | 200-300 mg Twice daily peroral | MW-144.12 Log P-0.62 |
| Fingolimod (FTY720) (Novartis) | SIP receptor modulator | Sphingosine 1-phosphate (SIP) activation | 0.25-0.5 mg Twice Daily peroral | MW-307.47 Log P-5.25 |
| Anakinra Swedish Orphan Biovitrum (Sobi) | Recombinant IL-1 receptor blocker | Reduce IL-1 pro-inflammatory activity | 100 mg IV Twice daily intravenous | MW-509.55 Log P-2.69 |
| Ebselen (PZ51, DR3305, SPI-1005) (Sound Therapeutics) | Anti-inflammatory | mimic of glutathione peroxidase | 400-600 mg Twice daily peroral | MW-244.17 Log P-2.65 |
| Ticareglor (Brilinta) (AstraZeneca) | platelet aggregation inhibitor | Reduce prothrombotic platelet activity | 30-90 mg Twice Daily peroral | MW-522.56 Log P-1.90 |
| Canakinumab (ACZ885, Haris) (Novartis) | IL-1 receptor blocker | Reduce IL-1 pro-inflammatory activity | 150-350 mg by SC injection | Monoclonal Antibody |
| Natalizumab (Tysabri) (Biogen) | anti-VLA-4 antibody | Blocking a4pi and a4p7 integrins | 300 mg Once daily intravenous | Monoclonal Antibody |
| sarilumab (Kevzara) (Sanofi, Regeneron) | IL-6 receptor blocker | Reduce IL-6 pro-inflammatory activity | 200 mg given by SC injection once | Monoclonal Antibody |

Dimethyl fumarate (DMF) is the methyl ester of fumaric acid and is named after the earth smoke plant (*Fumaria officinalis*). DMF combined with three other fumaric acid esters (FAEs) is solely licensed in Germany as an oral and is implicated in the pathogenesis of many diseases, such as autoimmune diseases, multiple myeloma and prostate cancer. It was developed by Hoffmann—La Roche and Chugai.

ADAMTS13, a protease that specifically cleaves VWF, 100 can be administered in vivo to reduce thrombosis and to aid in thrombolysis of thrombi in venules. Recombinant ADAMTS13 (rADAMTS13) can prevent microthrombosis such as in ischemia reperfusion injury occurring in myocardial infarction or stroke.

Ticagrelor (trade name Brilinta, Brilique, and formerly Possia) is a pharmaceutical drug used for the prevention of stroke, heart attack and other events in people with acute coronary syndrome, meaning problems with blood supply in the coronary arteries. It acts as a platelet aggregation inhibitor by antagonizing the P2Y12 receptor. The drug is produced by AstraZeneca.

Glycyrrhizin (OGC) (Glycyrrhizic acid) is the chief sweet-tasting constituent of *Glycyrrhiza glabra* (liquorice) root. Structurally, it is a saponin used as an emulsifier and gel-forming agent in foodstuffs and cosmetics. Its aglycone is enoxolone.

IV. 3,3'-Diindolylmethane ("DIM") or a DIM Analog for Use in Compositions and Methods The methods provided herein include use of 3,3'-diindolylmethane ("DIM"). As shown in FIGS. 1A-D, 2, 3A-C, 6 and 7, DIM reduces the formation of NETs, which have been implicated in the immunothrombotic etiology of AIS and AMI. In one embodiment, DIM is provided in a self microemulsifying drug delivery (SMEDDS) formulation. Such SMEDDS DIM formulations are known in the art, including those described herein in Examples 1-4, and disclosed in U.S. Pat. Nos. 9,928,965 and 10,441,569; and U.S. Patent Publication No. 2018/0280347.

In other embodiments, the methods provided herein include use of a DIM analog. DIM analogs include:

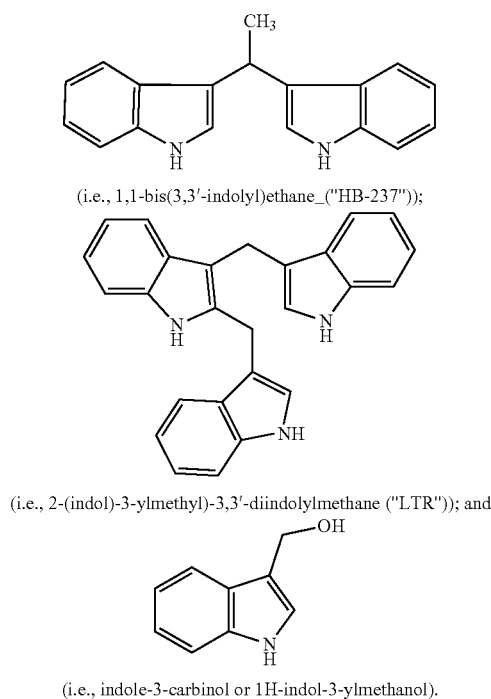 [SMILES: CC(c1c[nH]c2ccccc12)c1c[nH]c2ccccc12 ; c1ccc2c(Cc3[nH]c4ccccc4c3Cc3c[nH]c4ccccc34)c[nH]c2c1 ; OCc1c[nH]c2ccccc12]

(i.e., 1,1-bis(3,3'-indolyl)ethane_("HB-237"));

(i.e., 2-(indol)-3-ylmethyl)-3,3'-diindolylmethane ("LTR"); and (i.e., indole-3-carbinol or 1H-indol-3-ylmethanol).

It has been shown that indole-3-carbinol converts to DIM and LTR in vivo and in vitro. See, e.g., Anderton et al., Clin. Cancer Res. 10:5233-5241 (2004) and Bradlow et al. in vivo, 24:387-392 (2010).

V. Pharmaceutical Compositions

The pharmaceutical compositions provided herein contain therapeutically effective amounts of DIM or a DIM analog and/or a second active agent, and a pharmaceutically acceptable carrier, diluent or excipient.

The second active agents can be formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. Typically, the compounds described above are formulated into pharmaceutical compositions using techniques and procedures well known in the art (see, e.g., Ansel Introduction to Pharmaceutical Dosage Forms, Seventh Edition 1999).

In the compositions, effective concentrations of one or more second active agents and/or DIM or a DIM analog is (are) mixed with a suitable pharmaceutical carrier or vehicle. In certain embodiments, the concentrations of the second active agent and/or DIM or a DIM analog in the compositions are effective for delivery of an amount, upon administration, that treats, prevents, or ameliorates one or more of the symptoms and/or progression of a disease or disorder disclosed herein.

Typically, the compositions are formulated for single dosage administration. To formulate a composition, the weight fraction of compound is dissolved, suspended, dispersed or otherwise mixed in a selected vehicle at an effective concentration such that the treated condition is relieved or ameliorated. Pharmaceutical carriers or vehicles suitable for administration of the second active agent and/or DIM or a DIM analog include any such carriers known to those skilled in the art to be suitable for the particular mode of administration.

In addition, the second active agents and/or DIM or a DIM analog may be formulated as the sole pharmaceutically active ingredient in the composition or may be combined with other active ingredients. Liposomal suspensions, including tissue-targeted liposomes, such as lung-targeted liposomes, may also be suitable as pharmaceutically acceptable carriers. These may be prepared according to methods known to those skilled in the art. For example, liposome formulations may be prepared as known in the art. Briefly, liposomes such as multilamellar vesicles (MLV's) may be formed by drying down egg phosphatidyl choline and brain phosphatidyl serine (7:3 molar ratio) on the inside of a flask. A solution of a second active agent and/or DIM or a DIM analog in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

The second active agent and/or DIM or a DIM analog is included in the pharmaceutically acceptable carrier in an amount sufficient to exert a therapeutically useful effect in the absence of undesirable side effects on the subject treated. The therapeutically effective concentration may be determined empirically by testing the second active agent and/or DIM or a DIM analog in in vitro and in vivo systems described herein and then extrapolated therefrom for dosages for humans. In some embodiments, the second active agent and/or DIM or a DIM analog is administered in a method to achieve a therapeutically effective concentration of the drug.

The concentration of second active agent and/or DIM or a DIM analog in the pharmaceutical composition will depend on absorption, tissue distribution, inactivation and excretion rates of the second active agent and/or DIM or a DIM analog, the physicochemical characteristics of the second active agent and/or DIM or a DIM analog, the dosage schedule, and amount administered as well as other factors known to those of skill in the art. For example, the amount that is delivered is sufficient to ameliorate one or more of the symptoms of a disease or disorder disclosed herein.

In certain embodiments, a therapeutically effective dosage should produce a serum concentration of active ingredient of from about 0.1 ng/mL to about 50-100 μg/mL. In one embodiment, the pharmaceutical compositions provide a dosage of from about 0.001 mg to about 2000 mg of second active agent and/or DIM or a DIM analog per kilogram of body weight per day. Pharmaceutical dosage unit forms are prepared to provide from about 1 mg to about 1000 mg and in certain embodiments, from about 10 to about 500 mg of second active agent and/or DIM or a DIM analog per dosage unit form.

The active ingredient(s) may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

Thus, effective concentrations or amounts of one or more of the second active agents and/or DIM or a DIM analog are mixed with a suitable pharmaceutical carrier or vehicle for systemic, topical or local administration to form pharmaceutical compositions. Second active agents and/or DIM are included in an amount effective for ameliorating one or more symptoms of, or for treating, retarding progression, or preventing. The concentration of second active agent and/or DIM or a DIM analog in the composition will depend on absorption, tissue distribution, inactivation, excretion rates of the second active agent and/or DIM or a DIM analog, the dosage schedule, amount administered, particular formulation as well as other factors known to those of skill in the art.

The compositions are intended to be administered by a suitable route, including but not limited to oral, parenteral, subcutaneous, intravenous, intramuscular, intraperitoneal, intrathecal, mucosal, dermal, transdermal, buccal, rectal, topical, local, nasal or inhalation. For oral administration, capsules and tablets can be formulated. The compositions are in liquid, semi-liquid or solid form and are formulated in a manner suitable for each route of administration.

Solutions or suspensions used for parenteral, intradermal, subcutaneous, or topical application can include any of the following components: a sterile diluent, such as water for injection, saline solution, fixed oil, polyethylene glycol, glycerin, propylene glycol, dimethyl acetamide or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampules, pens, disposable syringes or single or multiple dose vials made of glass, plastic or other suitable material.

In instances in which the second active agents and/or DIM or a DIM analog exhibit insufficient solubility, methods for solubilizing the second active agent and/or DIM or a DIM analog may be used. Such methods are known to those of skill in this art, and include, but are not limited to, using cosolvents, such as dimethylsulfoxide (DMSO), using surfactants such as TWEEN®, or dissolution in aqueous sodium bicarbonate. In one embodiment, the second active agent and/or DIM or a DIM analog is formulated in a SMEDDS formulation.

Upon mixing or addition of the second active agent and/or DIM or a DIM analog, the resulting mixture may be a solution, suspension, emulsion or the like. The form of the resulting mixture depends upon a number of factors, including the intended mode of administration and the solubility of the second active agent and/or DIM or a DIM analog in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil water emulsions containing suitable quantities of the second active agent and/or DIM or a DIM analog. The second active agent and/or DIM or a DIM analog are formulated and administered in unit dosage forms or multiple dosage forms. Unit dose forms as used herein refer to physically discrete units suitable for human and animal subjects and packaged individually as is known in the art. Each unit dose contains a predetermined quantity of the second active agent and/or DIM or a DIM analog sufficient to produce the desired therapeutic effect, in association with the required pharmaceutical carrier, vehicle or diluent. Examples of unit dose forms include ampules and syringes and individually packaged tablets or capsules. Unit dose forms may be administered in fractions or multiples thereof. A multiple dose form is a plurality of identical unit dosage forms packaged in a single container to be administered in segregated unit dose form. Examples of multiple dose forms include vials, bottles of tablets or capsules or bottles of pints or gallons. Hence, multiple dose form is a multiple of unit doses which are not segregated in packaging.

Sustained-release preparations can also be prepared. Suitable examples of sustained-release preparations include semipermeable matrices of solid hydrophobic polymers containing the second active agent and/or DIM or a DIM analog, which matrices are in the form of shaped articles, e.g., films, or microcapsule. Examples of sustained-release matrices include iontophoresis patches, polyesters, hydrogels (for example, poly(2-hydroxyethyl-methacrylate), or poly(vinyl-alcohol)), polylactides, copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated second active agent and/or DIM or a DIM analog remains in the body for a long time, they may denature or aggregate as a result of exposure to moisture at 37° C., resulting in a loss of biological activity and possible changes in their structure. Rational strategies can be devised for stabilization depending on the mechanism of action involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Dosage forms or compositions containing active ingredient in the range of 0.005% to 100% with the balance made up from non-toxic carrier may be prepared. For oral administration, a pharmaceutically acceptable non-toxic composition is formed by the incorporation of any of the normally employed excipients, such as, for example pharmaceutical grades of mannitol, lactose, starch, magnesium stearate, talcum, cellulose derivatives, sodium croscarmellose, glucose, sucrose, magnesium carbonate or sodium saccharin. Such compositions include solutions, suspensions, tablets, capsules, powders and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of these compositions are known to those skilled in the art. The contemplated compositions may contain about 0.001% 100% active ingredient, in certain embodiments, about 0.1 85% or about 75-95%.

The second active agents and/or DIM or a DIM analog may be prepared with carriers that protect the second active agent and/or DIM or a DIM analog against rapid elimination from the body, such as time release formulations or coatings.

The compositions may include other active compounds to obtain desired combinations of properties. The second active agents and/or DIM or a DIM analog may also be advantageously administered for therapeutic or prophylactic purposes together with another pharmacological agent known in the general art to be of value in treating one or more of the diseases or medical conditions referred to hereinabove, such as diseases related to oxidative stress. It is to be understood that such combination therapy constitutes a further aspect of the compositions and methods of treatment provided herein.

Lactose-free compositions provided herein can contain excipients that are well known in the art and are listed, for example, in the U.S. Pharmacopeia (USP) SP (XXI)/NF (XVI). In general, lactose-free compositions contain an active ingredient, a binder/filler, and a lubricant in pharmaceutically compatible and pharmaceutically acceptable amounts. Exemplary lactose-free dosage forms contain an active ingredient, microcrystalline cellulose, pre-gelatinized starch and magnesium stearate.

Further encompassed are anhydrous pharmaceutical compositions and dosage forms containing a second active agent and/or DIM. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, Drug Stability: Principles & Practice, 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment and use of formulations.

Anhydrous pharmaceutical compositions and dosage forms provided herein can be prepared using anhydrous or low moisture containing ingredients and low moisture or low humidity conditions. Pharmaceutical compositions and dosage forms that comprise lactose and at least one active ingredient that comprises a primary or secondary amine are anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs and strip packs.

A. Oral Dosage Forms

Oral pharmaceutical dosage forms are either solid, gel or liquid. The solid dosage forms are tablets, capsules, granules, and bulk powders. Types of oral tablets include compressed, chewable lozenges and tablets which may be enteric coated, sugar coated or film coated. Capsules may be hard or soft gelatin capsules, while granules and powders may be provided in non-effervescent or effervescent form with the combination of other ingredients known to those skilled in the art.

In certain embodiments, the formulations are solid dosage forms, such as capsules or tablets. The tablets, pills, capsules, troches and the like can contain any of the following ingredients, or compounds of a similar nature: a binder; a diluent; a disintegrating agent; a lubricant; a glidant; a sweetening agent; and a flavoring agent.

Examples of binders include microcrystalline cellulose, gum tragacanth, glucose solution, acacia mucilage, gelatin solution, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include croscarmellose sodium, crospovidone, sodium starch glycolate, alginic acid, corn starch, potato starch, bentonite, methylcellulose, agar and carboxymethylcellulose. Coloring agents include, for example, any of the approved certified water-soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene lauryl ether. Enteric coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

If oral administration is desired, the second active agent and/or DIM or a DIM analog could be provided in a composition that protects it from the acidic environment of the stomach. For example, the composition can be formulated in an enteric coating that maintains its integrity in the stomach and releases the second active agent and/or DIM or a DIM analog in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The second active agent and/or DIM or a DIM analog can also be administered as a component of an elixir, suspension, syrup, wafer, sprinkle, chewing gum or the like. A syrup may contain, in addition to the second active agent and/or DIM or a DIM analog, sucrose as a sweetening agent and certain preservatives, dyes and colorings and flavors.

The second active agent and/or DIM or a DIM analog can also be mixed with other active materials which do not impair the desired action, or with materials that supplement the desired action, such as antacids, H2 blockers, and diuretics. Higher concentrations, up to about 98% by weight of the active ingredient may be included.

Pharmaceutically acceptable carriers included in tablets are binders, lubricants, diluents, disintegrating agents, coloring agents, flavoring agents, and wetting agents. Enteric coated tablets, because of the enteric coating, resist the action of stomach acid and dissolve or disintegrate in the neutral or alkaline intestines. Sugar coated tablets are compressed tablets to which different layers of pharmaceutically acceptable substances are applied. Film coated tablets are compressed tablets which have been coated with a polymer or other suitable coating. Multiple compressed tablets are compressed tablets made by more than one compression cycle utilizing the pharmaceutically acceptable substances previously mentioned. Coloring agents may also be used in the above dosage forms. Flavoring and sweetening agents are used in compressed tablets, sugar coated, multiple compressed and chewable tablets. Flavoring and sweetening agents are especially useful in the formation of chewable tablets and lozenges.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil in-water or water in oil. In some embodiments, the suspension is a suspension of microparticles or nanoparticles. In some embodiments, the emulsion is an emulsion of microparticles or nanoparticles.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic acid, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Diluents include lactose and sucrose. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water-soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi solid oral formulations may be prepared by dissolving or dispersing the second active agent and/or DIM or a DIM analog in vegetable oils, glycols, triglycerides, propylene glycol esters (e.g., propylene carbonate) and other such carriers, and encapsulating these solutions or suspensions in hard or soft gelatin capsule shells. Other useful formulations include, but are not limited to, those containing a second active agent and/or DIM, a dialkylated mono- or poly-alkylene glycol, including, but not limited to, 1,2-dimethoxyethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

B. Injectables, Solutions and Emulsions

Parenteral administration, generally characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions, including SMEDDS formulations. In some embodiments, the suspension is a suspension of microparticles or nanoparticles. In some embodiments, the emulsion is an emulsion of microparticles or nanoparticles. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. Implantation of a slow release or sustained release system, such that a constant level of dosage is maintained is also contemplated herein. Briefly, a second active agent and/or DIM or a DIM analog is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The second active agent and/or DIM or a DIM analog diffuses through the outer polymeric membrane in a release rate controlling step. The percentage of second active agent and/or DIM or a DIM analog contained in such parenteral compositions is highly dependent on the specific nature thereof, as well as the activity of the second active agent and/or DIM or a DIM analog and the needs of the subject.

Parenteral administration of the compositions includes intravenous, intraarterial, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple dose containers which include phenols or cresols, mercurials, benzyl alcohol, chlorobutanol, methyl and propyl p hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles and sodium hydroxide, hydrochloric acid, citric acid or lactic acid for pH adjustment.

The concentration of the second active agent and/or DIM or a DIM analog is adjusted so that an injection provides an effective amount to produce the desired pharmacological effect. The exact dose depends on the age, weight and condition of the subject or animal as is known in the art.

The unit dose parenteral preparations are packaged in an ampule, a vial or a syringe with a needle. All preparations for parenteral administration must be sterile, as is known and practiced in the art.

Illustratively, intravenous or intraarterial infusion of a sterile aqueous solution containing a second active agent and/or DIM or a DIM analog is an effective mode of administration. Another embodiment is a sterile aqueous or oily solution or suspension containing an active material injected as necessary to produce the desired pharmacological effect.

Injectables are designed for local and systemic administration. Typically, a therapeutically effective dosage is formulated to contain a concentration of at least about 0.1% w/w up to about 90% w/w or more, such as more than 1% w/w of the second active agent and/or DIM or a DIM analog to the treated tissue(s). The active ingredient may be administered at once, or may be divided into a number of smaller doses to be administered at intervals of time. It is understood that the precise dosage and duration of treatment is a function of the tissue being treated and may be determined empirically using known testing protocols or by extrapolation from in vivo or in vitro test data. It is to be noted that concentrations and dosage values may also vary with the age of the individual treated. It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope or practice of the claimed formulations.

The second active agent and/or DIM or a DIM analog may be suspended in micronized or other suitable form or may be derivatized to produce a more soluble active product or to produce a prodrug. The form of the resulting mixture depends upon a number of factors, including the intended mode of administration and the solubility of the second active agent and/or DIM or a DIM analog in the selected carrier or vehicle. The effective concentration is sufficient for ameliorating the symptoms of the condition and may be empirically determined.

In another embodiment, provided are IV formulations of DIM or a DIM analog containing one or more of anhydrous ethanol, polyoxyl castor oil, phosphatidyl choline, oleoyl polyoxyl-6 glycerides and poly(ethylene glycol)-block-poly(propylene glycol)-block-poly(ethylene glycol) copolymer. In another embodiment, the IV formulations contain DIM. In another embodiment, the IV formulations contain 10% DIM, 43% anhydrous ethanol, 19% polyoxyl castor oil, 8% phosphatidyl choline, 9% oleoyl polyoxyl-6 glycerides and 11% poly(ethylene glycol)-block-poly(propylene glycol)-block-poly(ethylene glycol) copolymer. In further embodiments, the polyoxyl castor oil is BASF Kolliphor® EL. In another embodiment, the oleoyl polyoxyl-6 glycerides are Gattefosse LABRAFIL® M1944 CS. In another embodiment, the poly(ethylene glycol)-block-poly(propylene glycol)-block-poly(ethylene glycol) copolymer is BASF Poloxamer 188. In another embodiment, the IV formulations contain 10% 3,3'-diindolylmethane, 43% anhydrous ethanol, 19% BASF Kolliphor® EL, 8% Phosphatidyl Choline, 9% Gattefosse LABRAFIL® M1944 CS, and 11% BASF Poloxamer 188.

In another embodiment, provided are IV formulations of DIM or a DIM analog containing one or more of anhydrous ethanol, medium chain triglycerides, phosphatidyl choline, polyoxyl 15 hydroxystearate, and one or more poly(ethylene glycol)-block-poly(propylene glycol)-block-poly(ethylene glycol) copolymers. In another embodiment, the IV formulations contain DIM. In another embodiment, the IV formulations contain 2% DIM, 45% anhydrous ethanol, 10% medium chain triglycerides, 8% phosphatidyl choline, 15% polyoxyl 15 hydroxystearate, and 20% of one or more poly(ethylene glycol)-block-poly(propylene glycol)-block-poly(ethylene glycol) copolymers. In another embodiment, the medium chain triglycerides are Gattefosse WL 1349. In another embodiment, the polyoxyl 15 hydroxystearate is BASF HS-15. In another embodiment, the one or more poly(ethylene glycol)-block-poly(propylene glycol)-block-poly(ethylene glycol) copolymers are poloxamer 188 and/or poloxamer 407. In another embodiment, the IV formulations contain 2% DIM, 45% anhydrous ethanol, 10% Gattefosse WL 1349, 8% phosphatidyl choline, 15% BASF HS-15, 8% poloxamer 188 and 12% poloxamer 407.

C. Lyophilized Powders

Of interest herein are also lyophilized powders, which can be reconstituted for administration as solutions, emulsions and other mixtures. They may also be reconstituted and formulated as solids or gels.

The sterile, lyophilized powder is prepared by dissolving a second active agent and/or DIM or a DIM analog in a suitable solvent. The solvent may contain an excipient which improves the stability or other pharmacological component of the powder or reconstituted solution, prepared from the powder. Excipients that may be used include, but are not limited to, dextrose, sorbitol, fructose, corn syrup, xylitol, glycerin, glucose, sucrose or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. Generally, the resulting solution will be apportioned into vials for lyophilization. Each vial will contain a single dosage (including but not limited to 10-1000 mg or 100-500 mg) or multiple dosages of the second active agent and/or DIM. The lyophilized powder can be stored under appropriate conditions, such as at about 4° C. to room temperature.

Reconstitution of this lyophilized powder with water for injection provides a formulation for use in parenteral administration. For reconstitution, about 1-50 mg, about 5-35 mg, or about 9-30 mg of lyophilized powder, is added per mL of sterile water or other suitable carrier. The precise amount depends upon the selected second active agent and/or DIM. Such amount can be empirically determined.

D. Compositions for Other Routes of Administration

Other routes of administration, such as transdermal patches, and rectal administration are also contemplated herein.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin gelatin, carbowax (polyoxyethylene glycol) and appropriate mixtures of mono, di and triglycerides of fatty acids. Combinations of the various bases may be used. Agents to raise the melting point of suppositories include spermaceti and wax. Rectal suppositories may be prepared either by the compressed method or by molding. An exemplary weight of a rectal suppository is about 2 to 3 grams.

Tablets and capsules for rectal administration are manufactured using the same pharmaceutically acceptable substance and by the same methods as for formulations for oral administration.

In one embodiment, DIM or a DIM analog is provided in a parenteral microdispersion for intra-arterial administration to make direct contact with a thrombus during EVT for AIS. The microdispersed DIM or DIM analog is infused by hand-controlled injection into specialized mechanical thrombectomy catheters which are described in U.S. Patent Publication No. US 2020/0129192 A1 by Lin. Injection is made when the distal orifice of the thrombectomy catheter is positioned radiographically in close proximity to the occluding thrombus. In an alternative embodiment, the surfaces of thrombectomy catheters and stent retriever apparatus are coated with DIM or a DIM analog according to methods described in U.S. Patent Publication No. US 2017/0143663 A1 by Yamashita et al. Coating methods of Yamashita et al. are adapted to utilize DIM or a DIM analog as the water insoluble API incorporated in the coating matrix which is applied to MT devices which elute DIM or a DIM analog into the bloodstream during EVT.

E. Sustained Release Compositions

Active ingredients provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, 5,639,480, 5,733,566, 5,739,108, 5,891,474, 5,922,356, 5,972,891, 5,980,945, 5,993,855, 6,045,830, 6,087,324, 6,113,943, 6,197,350, 6,248,363, 6,264,970, 6,267,981, 6,376,461, 6,419,961, 6,589,548, 6,613,358, 6,699,500 and 6,740,634, each of which is incorporated herein by reference. Such dosage forms can be used to provide slow or controlled-release of one or more active ingredients using, for example, hydroxypropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients provided herein.

All controlled-release pharmaceutical products have a common goal of improving drug therapy over that achieved by their non-controlled counterparts. In one embodiment, the use of an optimally designed controlled-release preparation in medical treatment is characterized by a minimum of drug substance being employed to cure or control the condition in a minimum amount of time. In certain embodiments, advantages of controlled-release formulations include extended activity of the drug, reduced dosage frequency, and increased subject compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled release of an active ingredient can be stimulated by various conditions including, but not limited to, pH, temperature, enzymes, water, or other physiological conditions or compounds.

In certain embodiments, the agent may be administered using intravenous infusion, an implantable osmotic pump, a transdermal patch, liposomes, or other modes of administration. In one embodiment, a pump may be used (see, Sefton, CRC Crit. Ref. Biomed. Eng. 14:201 (1987); Buchwald et al., Surgery 88:507 (1980); Saudek et al., N. Engl. J. Med. 321:574 (1989). In another embodiment, polymeric materials can be used. In yet another embodiment, a controlled release system can be placed in proximity of the therapeutic target, i.e., thus requiring only a fraction of the systemic dose (see, e.g., Goodson, Medical Applications of Controlled Release, vol. 2, pp. 115-138 (1984).

In some embodiments, a controlled release device is introduced into a subject in proximity of the site of inappropriate immune activation or a tumor. Other controlled release systems are discussed in the review by Langer (Science 249:1527-1533 (1990). The active ingredient can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of active ingredient contained in such parenteral compositions is highly dependent on the specific nature thereof, as well as the needs of the subject.

F. Targeted Formulations

The second active agent and/or DIM or a DIM analog may also be formulated to be targeted to a particular tissue, receptor, or other area of the body of the subject to be treated, including liposome-, resealed erythrocyte-, and antibody-based delivery systems. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874.

In one embodiment, the antibody-based delivery system is an antibody-drug conjugate ("ADC"), e.g., as described in Hamilton G S, Biologicals, 2015 September, 43(5):318-32; Kim E G and Kim K M, Biomol. Ther. (Seoul), 2015 November, 23(6):493-509; and Peters C and Brown S, Biosci. Rep., 2015 Jun. 12, 35(4) pii: e00225, each of which is incorporated herein by reference.

In one embodiment, liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a second active agent and/or DIM or a DIM analog in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

G. Articles of Manufacture

The second active agent and/or DIM or a DIM analog can be packaged as articles of manufacture containing packaging material, a second active agent and/or DIM, which is used for treatment, prevention or amelioration of one or more symptoms or progression of a disease or disorder disclosed herein, and a label that indicates that the second active agent and/or DIM or a DIM analog is used for treatment, prevention or amelioration of one or more symptoms or progression of a disease or disorder disclosed herein.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, pens, bottles, and any packaging material suitable for a selected formulation and intended mode of administration and treatment. A wide array of formulations of the second active agent and/or DIM or a DIM analog and compositions provided herein are contemplated.

In certain embodiments, provided herein also are kits which, when used by the medical practitioner, can simplify the administration of appropriate amounts of active ingredients to a subject. In certain embodiments, the kit provided herein includes a container and a dosage form of a second active agent and/or DIM. For use in kits for oral administration to AIS and ACS patients by EMT first responders and Emergency Room physicians, DIM is included in BR9001 capsules providing 200-500 mg. Embodiments of kits providing DIM and a second active agent for oral use in the setting of AIS and Acute Coronary Syndrome (ACM) include the following Second Active Agents administered as soon as possible after the onset of symptoms:

| Second Active Agent | Manufacturer | Dose Range |
| --- | --- | --- |
| Colchicine | Generic | 1.5-4.5 mg |
| Chloroquine phosphate | Generic | 250-750 mg (150-450 mg-base) |
| All Trans Retinoic Acid (ATRA) (Vesanoid ®) | Roche | 10-40 mg |
| Glycyrrhizin (OGC) (Glycyrrhizic acid) | Minophagen Pharmaceutical Co. Ltd. | 40-200 mg |
| LPN023 | Novartis | 200-400 mg |
| CCX168 (avacopan) | ChemoCentrys | 10-40 mg |
| ACH0144471 | Achillion | 100-200 mg |
| ACH145951 | Achillion | 50-200 mg |
| JNJ-70033093 Previously BMS986177 | Johnson and Johnson (J & J) | 25-200 mg |

In certain embodiments, the kit includes a container comprising a dosage form of the second active agent and/or DIM or a DIM analog in a container comprising one or more other therapeutic agent(s) described herein.

Kits provided herein can further include devices that are used to administer the active ingredients. Examples of such devices include, but are not limited to, syringes, needle-less injectors drip bags, patches, and inhalers. The kits provided herein can also include condoms for administration of the active ingredients.

Kits provided herein can further include pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: aqueous vehicles, including, but not limited to, Water for Injection USP, Sodium Chloride Injection, Ringer's Injection, Dextrose Injection, Dextrose and Sodium Chloride Injection, and Lactated Ringer's Injection; water-miscible vehicles, including, but not limited to, ethyl alcohol, polyethylene glycol, and polypropylene glycol; and non-aqueous vehicles, including, but not limited to, corn oil, cottonseed oil, peanut oil, sesame oil, ethyl oleate, isopropyl myristate, and benzyl benzoate.

VI. Dosing

The second active agent and/or DIM or a DIM analog and pharmaceutical compositions provided herein may be dosed in certain therapeutically or prophylactically effective amounts, certain time intervals, certain dosage forms, and certain dosage administration methods as described below.

In certain embodiments, a therapeutically or prophylactically effective amount of the second active agent and/or DIM or a DIM analog is from about 0.005 to about 1,000 mg per day, from about 0.01 to about 500 mg per day, from about 0.01 to about 250 mg per day, from about 0.01 to about 100 mg per day, from about 0.1 to about 100 mg per day, from about 0.5 to about 100 mg per day, from about 1 to about 100 mg per day, from about 0.01 to about 50 mg per day, from about 0.1 to about 50 mg per day, from about 0.5 to about 50 mg per day, from about 1 to about 50 mg per day, from about 0.02 to about 25 mg per day, from about 0.05 to about 10 mg per day, from about 0.05 to about 5 mg per day, from about 0.1 to about 5 mg per day, or from about 0.5 to about 5 mg per day.

In certain embodiments, the therapeutically or prophylactically effective amount is about 0.1, about 0.2, about 0.5, about 1, about 2, about 3, about 4, about 5, about 6, about 7, about 8, about 9, about 10, about 15, about 20, about 25, about 30, about 40, about 45, about 50, about 60, about 70, about 80, about 90, about 100, or about 150 mg per day.

In one embodiment, the recommended daily dose range of the second active agent and/or DIM or a DIM analog for the conditions described herein lie within the range of from about 0.5 mg to about 50 mg per day, in one embodiment given as a single once-a-day dose, or in divided doses throughout a day. In some embodiments, the dosage ranges from about 1 mg to about 50 mg per day. In other embodiments, the dosage ranges from about 0.5 to about 5 mg per day. Specific doses per day include 0.1, 0.2, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 mg per day.

In a specific embodiment, the recommended starting dosage may be 0.5, 1, 2, 3, 4, 5, 10, 15, 20, 25 or 50 mg per day. In another embodiment, the recommended starting dosage may be 0.5, 1, 2, 3, 4, or 5 mg per day. The dose may be escalated to 15, 20, 25, 30, 35, 40, 45 and 50 mg/day. In a specific embodiment, the second active agent and/or DIM or a DIM analog can be administered in an amount of about 25 mg/day. In a particular embodiment, the second active agent and/or DIM or a DIM analog can be administered in an amount of about 10 mg/day. In a particular embodiment, the second active agent and/or DIM or a DIM analog can be administered in an amount of about 5 mg/day. In a particular embodiment, the second active agent and/or DIM or a DIM analog can be administered in an amount of about 4 mg/day. In a particular embodiment, the second active agent and/or DIM or a DIM analog can be administered in an amount of about 3 mg/day.

In certain embodiments, the therapeutically or prophylactically effective amount is from about 0.001 to about 100 mg/kg/day, from about 0.01 to about 50 mg/kg/day, from about 0.01 to about 25 mg/kg/day, from about 0.01 to about 10 mg/kg/day, from about 0.01 to about 9 mg/kg/day, 0.01 to about 8 mg/kg/day, from about 0.01 to about 7 mg/kg/day, from about 0.01 to about 6 mg/kg/day, from about 0.01 to about 5 mg/kg/day, from about 0.01 to about 4 mg/kg/day, from about 0.01 to about 3 mg/kg/day, from about 0.01 to about 2 mg/kg/day, from about 0.01 to about 1 mg/kg/day, or from about 0.01 to about 0.05 mg/kg/day.

The dosage and administration of pharmaceutical compositions of DIM or a DIM analog in the clinical setting of AIS and AMI are guided by the presenting condition of the patient and current standard of care guidelines. For conscious patients with symptoms of AIS with imaging confirmation of absence of intracranial hemorrhage based on Computerized Tomography (CT) or Magnetic Resonance Imaging (MRI), oral administration is preferred as soon as possible before EVT. In one embodiment, the composition and dosage is a SMEDDS DIM formulation providing 200-500 mg DIM per oral administration, repeated after 4-8 hours three times and thereafter every 12 hours for 3-5 days. For AIS patients who are stuporous or sedated, intravenous (IV) administration of DIM is from a micro-suspension of DIM (e.g., Example 4). In one embodiment, the dosage of IV DIM is from 50-200 mg DIM administered with a 30-minute infusion, repeated after 4-8 hours three times and thereafter every 12 hours for up to 3-5 days. For patients with symptoms of AMI who are candidates for PTCA, the same administration and dosage guidelines for peroral DIM are appropriate as soon as possible before procedural sedation. For patients with evidence of LVO thrombosis diagnosed during cerebral or coronary angiography, DIM or a DIM analog is in one embodiment administered intravenously immediately prior to MT. In other embodiments, oral and IV compositions of DIM are administered when used in conjunction with tPA (Activase (alteplase)) or related Tenecteplase (TNKASE®) with or without EVT and MT. In addition, oral and IV compositions of DIM are used in the clinical settings of AIS and AMI without tPA when some of the contraindications to the use of tPA exist. Common contraindications for tPA and Tenecteplase use include active recent (within 3 months) intracranial or intraspinal surgery or serious head trauma, presence of intracranial conditions that may increase the risk of bleeding (e.g., some neoplasms, arteriovenous malformations, or aneurysms), and current severe uncontrolled hypertension. In certain patients with AIS or AMI the DIM or a DIM analog is administered intra-arterially at the site of arterial thrombosis and large vessel occlusion (LVO) using a mg dose of DIM or a DIM analog and rate of infusion to be determined and ordered by the attending physician.

The administered dose of DIM or a DIM analog can also be expressed in units other than mg/kg/day. For example, doses for parenteral administration can be expressed as mg/m2/day. One of ordinary skill in the art would readily know how to convert doses from mg/kg/day to mg/m2/day to given either the height or weight of a subject or both (see, www.fda.gov/cder/cancer/animalframe.htm). For example, a dose of 1 mg/kg/day for a 65 kg human is approximately equal to 38 mg/m2/day.

In certain embodiments, the amount of the second active agent and/or DIM or a DIM analog administered is sufficient to provide a plasma concentration of the second active agent and/or DIM or a DIM analog at steady state, ranging from about 0.001 to about 500 about 0.002 to about 200 about 0.005 to about 100 about 0.01 to about 50 from about 1 to about 50 about 0.02 to about 25 from about 0.05 to about 20 from about 0.1 to about 20 from about 0.5 to about 20 or from about 1 to about 20 µM.

In other embodiments, the amount of the second active agent and/or DIM or a DIM analog administered is sufficient to provide a plasma concentration of the second active agent and/or DIM or a DIM analog at steady state, ranging from about 5 to about 100 nM, about 5 to about 50 nM, about 10 to about 100 nM, about 10 to about 50 nM or from about 50 to about 100 nM.

As used herein, the term "plasma concentration at steady state" is the concentration reached after a period of administration of a second active agent and/or DIM or a DIM analog. Once steady state is reached, there are minor peaks and troughs on the time dependent curve of the plasma concentration of the second active agent and/or DIM or a DIM analog.

In certain embodiments, the amount of the second active agent and/or DIM or a DIM analog administered is sufficient to provide a maximum plasma concentration (peak concentration) of the second active agent and/or DIM or a DIM analog, ranging from about 0.001 to about 50 about 0.002 to about 200 about 0.005 to about 100 about 0.01 to about 50 from about 1 to about 50 about 0.02 to about 25 from about 0.05 to about 20 from about 0.1 to about 20 from about 0.5 to about 20 or from about 1 to about 20 µM.

In certain embodiments, the amount of the second active agent and/or DIM or a DIM analog administered is sufficient to provide a minimum plasma concentration (trough concentration) of the second active agent and/or DIM, ranging from about 0.001 to about 500 about 0.002 to about 200 about 0.005 to about 100 about 0.01 to about 50 from about 1 to about 50 about 0.01 to about 25 from about 0.01 to about 20 from about 0.02 to about 20 from about 0.02 to about 20 or from about 0.01 to about 20 µM.

In certain embodiments, the amount of the second active agent and/or DIM or a DIM analog administered is sufficient to provide an area under the curve (AUC) of the second active agent and/or DIM, ranging from about 100 to about 100,000 ng*hr/mL, from about 1,000 to about 50,000 ng*hr/mL, from about 5,000 to about 25,000 ng*hr/mL, or from about 5,000 to about 10,000 ng*hr/mL.

The methods provided herein encompass treating a patient regardless of subject's age, although some diseases or disorders are more common in certain age groups.

Depending on the disease to be treated and the subject's condition, the second active agent and/or DIM or a DIM analog may be administered by oral, parenteral (e.g., intramuscular, intraperitoneal, intravenous, CIV, intracisternal injection or infusion, subcutaneous injection, or implant), inhalation, nasal, vaginal, rectal, sublingual, or topical (e.g., transdermal or local) routes of administration. The second active agent and/or DIM or a DIM analog may be formulated, alone or together, in suitable dosage unit with pharmaceutically acceptable excipients, carriers, adjuvants and vehicles, appropriate for each route of administration.

In one embodiment, the second active agent and/or DIM or a DIM analog is administered orally. In another embodiment, the second active agent and/or DIM or a DIM analog is administered parenterally. In yet another embodiment, the second active agent and/or DIM or a DIM analog is administered intravenously.

The second active agent and/or DIM or a DIM analog can be delivered as a single dose such as, e.g., a single bolus injection, or oral tablets or pills; or over time, such as, e.g., continuous infusion over time or divided bolus doses over time. The second active agent and/or DIM or a DIM analog can be administered repeatedly if necessary, for example, until the subject experiences stable disease or regression, or until the subject experiences disease progression or unacceptable toxicity. For example, stable disease for solid tumors generally means that the perpendicular diameter of measurable lesions has not increased by 25% or more from the last measurement. Response Evaluation Criteria in Solid Tumors (RECIST) Guidelines, Journal of the National Cancer Institute 92(3): 205 216 (2000). Stable disease or lack thereof is determined by methods known in the art such as evaluation of patient symptoms, physical examination, visualization of the tumor that has been imaged using X-ray, CAT, PET, or MRI scan and other commonly accepted evaluation modalities.

The second active agent and/or DIM or a DIM analog can be administered once daily (QD), or divided into multiple daily doses such as twice daily (BID), three times daily (TID), and four times daily (QID). In addition, the administration can be continuous (i.e., daily for consecutive days or every day), intermittent, e.g., in cycles (i.e., including days, weeks, or months of rest without drug). As used herein, the term "daily" is intended to mean that a therapeutic compound, such as the second active agent and/or DIM or a DIM analog is administered once or more than once each day, for example, for a period of time. The term "continuous" is intended to mean that a therapeutic compound, such as the second active agent and/or DIM or a DIM analog is administered daily for an uninterrupted period of at least 10 days to 52 weeks. The term "intermittent" or "intermittently" as used herein is intended to mean stopping and starting at either regular or irregular intervals. For example, intermittent administration of the second active agent and/or DIM or a DIM analog is administration for one to six days per week, administration in cycles (e.g., daily administration for two to eight consecutive weeks, then a rest period with no administration for up to one week), or administration on alternate days. The term "cycling" as used herein is intended to mean that a therapeutic compound, such as the second active agent and/or DIM or a DIM analog is administered daily or continuously but with a rest period. In some such embodiments, administration is once a day for two to six days, then a rest period with no administration for five to seven days.

In some embodiments, the frequency of administration is in the range of about a daily dose to about a monthly dose. In certain embodiments, administration is once a day, twice a day, three times a day, four times a day, once every other day, twice a week, once every week, once every two weeks, once every three weeks, or once every four weeks. In one embodiment, the second active agent and/or DIM or a DIM analog is administered once a day. In another embodiment, the second active agent and/or DIM or a DIM analog is administered twice a day. In yet another embodiment, the second active agent and/or DIM or a DIM analog is administered three times a day. In still another embodiment, the second active agent and/or DIM or a DIM analog is administered four times a day.

In certain embodiments, the second active agent and/or DIM or a DIM analog is administered once per day from one day to six months, from one week to three months, from one week to four weeks, from one week to three weeks, or from one week to two weeks. In certain embodiments, the second active agent and/or DIM or a DIM analog is administered once per day for one week, two weeks, three weeks, or four weeks. In one embodiment, the second active agent and/or DIM or a DIM analog is administered once per day for 4 days. In one embodiment, the second active agent and/or DIM or a DIM analog is administered once per day for 5 days. In one embodiment, the second active agent and/or DIM or a DIM analog is administered once per day for 6 days. In one embodiment, the second active agent and/or DIM or a DIM analog is administered once per day for one week. In another embodiment, the second active agent and/or DIM or a DIM analog is administered once per day for two weeks. In yet another embodiment, the second active agent and/or DIM or a DIM analog is administered once per day for three weeks. In still another embodiment, the second active agent and/or DIM or a DIM analog is administered once per day for four weeks.

VII. Examples

The examples below are meant to illustrate certain embodiments provided herein, and not to limit the scope of this disclosure.

Example 1

SMEDDS DIM Formulation; BR-9001; Placebo SMEDDS Vehicle

Method 1: The following were added to a small scintillation vial in the following order: 2.8 grams caprylocaproyl polyoxyl-8 glycerides (Gattefosse LABRASOL® ALF), 1.8 grams lauroyl polyoxyl 32 glycerides (Gattefosse GELUCIRE® 44/14), 2.4 grams poloxamer 124 (BASF, polyethylene-polypropylene glycol, CAS RN 9003-11-6, $HO(C_2H_4O)_a(C_3H_6O)_b(C_2H_4O)_aH$), 1.0 grams oleoyl polyoxyl-6 glycerides (Gattefosse LABRAFIL® M1944CS). The mixture was warmed and gently agitated to uniformity. 0.8 Grams of phosphatidyl choline (Lipoid PHOSPHOLIPON® 90G) was added to the mixture with warming to approximately 70° C. After cooling to approximately 50° C., 1.2 grams of 3,3'-diindolylmethane (BioResponse, LLC) was added with continuing agitation until the mixture was uniform.

Method 2: Production method for BR-9001. Formula for BR-9001:

| Ingredient | Supplier | Percentage |
|---|---|---|
| GELUCIRE ® 44/14 | Gattefosse | 18.0% |
| LABRASOL ® ALF | Gattefosse | 28.0% |
| Poloxamer 124 | BASF | 24.0% |
| LABRAFIL ® M1944CS | Gattefosse | 10.0% |
| PHOSPHOLIPON ® 90G | Lipoid | 8.0% |
| 3,3'-diindolylmethane | BioResponse, LLC | 12.0% |
| Total | | 100.0% |

Containers of GELUCIRE® 44/14 and poloxamer 124 were placed in an oven or appropriate warming bath set at approximately 50° C. An appropriately sized container was equipped with overhead agitator and thermometer. Either a jacketed container was used or a hot plate was used to be able to heat the container. The GELUCIRE®, the poloxamer, the LABRASOL® ALF, and the LABRAFIL® M1944 CS were each added sequentially in this order to the container with stirring. The mixture was homogeneous. The mixture was heated to range of 50 to 60° C. with continued stirring. The granular PHOSPHOLIPON® 90G was stored refrigerated. It was removed from the refrigeration and allowed to come to room temperature before opening the container. The amount was weighed and added to the stirring container. Agitation was increased to appropriate speed so as not to entrain air. The mixture was stirred to uniformity which may take several hours at temperature. The mixture was allowed to cool to approximately 40 to 45° C. and the 3,3'-diindolylmethane was weighed and added with stirring. The container was covered in foil to keep out of direct light. The mixture was uniform within 30 minutes. The mixture can be stored in appropriate amber glass containers out of direct light.

Method 3: Placebo SMEDDS vehicle

| Ingredient | Supplier | Percentage |
|---|---|---|
| GELUCIRE ® 44/14 | Gattefosse | 20.45% |
| LABRASOL ® ALF | Gattefosse | 31.82% |
| Poloxamer 124 | BASF | 27.27% |
| LABRAFIL ® M1944CS | Gattefosse | 11.36% |
| PHOSPHOLIPON ® 90G | Lipoid | 9.10% |
| Total | | 100.0% |

The placebo was made the same way as in Method 2 above except for the addition of the DIM. The placebo mixture does not need to be covered with foil.

Example 2

SMEDDS DIM Formulation with Retinyl Palmitate or Tretinoin

The following were added to a small scintillation vial in the following order: 2.8 grams caprylocaproyl polyoxyl-8 glycerides (Gattefosse LABRASOL® ALF), 1.8 grams lauroyl polyoxyl 32 glycerides (Gattefosse GELUCIRE® 44/14), 2.4 grams poloxamer 124 (BASF, polyethylene-polypropylene glycol, CAS RN 9003-11-6, $HO(C_2H_4O)_a(C_3H_6O)_b(C_2H_4O)_aH)$, 0.8 grams oleoyl polyoxyl-6 glycerides (Gattefosse LABRAFIL® M1944CS). The mixture was warmed and gently agitated to uniformity. 0.8 Grams of phosphatidyl choline (Lipoid PHOSPHOLIPON® 90G) was added to the mixture with warming to approximately 80° C. After cooling to approximately 50° C., 1.2 grams of 3,3'-diindolylmethane (BioResponse, LLC) was added with continuing agitation until the mixture was uniform. In a separate small scintillation vial, a 100:1 dilution of retinyl palmitate was prepared by adding 100 mg of retinyl palmitate to 9.90 grams of oleoyl polyoxyl-6 glycerides (Gattefosse LABRAFIL® M1944CS). 200 mg of this dilution was added to the formulation representing 2.0 mg of retinyl palmitate and the mixture stirred to uniformity. Alternatively, tretinoin (all trans retinoic acid) is substituted for retinyl palmitate in the amounts specified above.

Example 3

SMEDDS DIM Formulation with Caproyl-90

In a manner similar to Examples 1 and 2, the following components were used to form a SMEDDS DIM formulation: 2.8 grams caprylocaproyl polyoxyl-8 glycerides (Gattefosse LABRASOL® ALF), 1.8 grams lauroyl polyoxyl 32 glycerides (Gattefosse Gelucire® 44/14), 2.4 grams poloxamer 124 (BASF, polyethylene-polypropylene glycol, CAS RN 9003-11-6, $HO(C_2H_4O)_a(C_3H_6O)_b(C_2H_4O)_aH)$, 1.0 grams oleoyl polyoxyl-6 glycerides (Gattefosse LABRAFIL® M1944CS), 0.4 grams of phosphatidyl choline (Lipoid PHOSPHOLIPON® 90G), 0.4 g caproyl-90 (propylene glycol mono- and diesters of caprylic acid, >90% monoester).

Example 4

Development of a Premix Formulation of 3,3'-Diindolylmethane (DIM) for Suspension in Physiologic Diluent and Intravenous Administration in Hospital Settings—an IV DIM Drug Product (BR2022 IV)

Hospital based management of AIS and AMI is associated with hypoxemia, respiratory distress, and the need for expedient EVT. AIS and AMI patients often have diminished level of consciousness and require "nothing by mouth (NPO)" status. For these reasons a DIM-specific intravenous formulation was developed to provide for efficient anti-NET therapy in hospitalized patients. The present formulation allows for ease of administration and for achieving the highest possible plasma and tissue levels of DIM during and following EVT. Typical dosage will be from 100-300 mg DIM given IV every 8 hours for up to 5 consecutive days.

After testing several formulation prototypes using a subset of DIM compatible excipients with a history of use in parenteral drug products, the following mixture was developed for the IV DIM Premix drug product. The prototype was produced, tested for stability of typical pre-administration dispersion, and made ready for further development for clinical trial application as an intravenous dosage form for DIM.

| Formula Wt % | Component Name | Function of Component |
|---|---|---|
| 10.0% | 3,3'-diindolylmethane | Active Pharmaceutical Ingredient (API) |
| 43% | Anhydrous ethanol | Premix solvent |
| 19% | BASF Kolliphor ® EL | Excipient |
| 8.0% | Phosphatidyl Choline | Emulsifier |
| 9% | Gattefosse LABRAFIL ® M1944 CS | Excipient |
| 11.0% | BASF Pol oxamer 188 | Excipient |

Steps in Production of the IV DIM Premix for Suspension in 0.9% NaCl or 5% Dextrose and Immediate IV Administration Ten (10) grams of the mix was prepared using the following procedure. A small vial equipped with a spin bar was used. To this was added the following in this order: 4.3 grams anhydrous ethanol, 1.0 grams 3,3'-diindolylmethane (DIM), 0.8 grams of phosphatidyl choline, 1.9 grams Kolliphor® EL (a.k.a. Cremophor EL; polyethoxylated castor oil, CAS No. 61791-12-6), 0.9 grams of Gattefosse LABRAFIL® M1944 CS, and 1.1 grams of BASF Poloxamer 188. The mixture was warmed to 45° C. in a water bath and stirred for 30 minutes. The resulting clear solution of IV DIM Premix was used for testing without further mixing.

Evaluation of the IV DIM Premix Drug Product Following Dispersion

Testing of the IV DIM Premix (BR2022 IV) was performed by addition of 1,000 mg of the above formulation to 0.5 L of water stirring in a 1 L beaker with a spin bar with sufficient speed to take the vortex almost to the bottom of the beaker. Stirring was discontinued after one minute. The Premix formulation dispersed uniformly through the suspension and appeared to be opalescent. Examination under a microscope showed that there were almost no visible drops or crystalline material in the suspension. After one hour of standing, crystals of about 2 to 5 microns were beginning to form as seen under a microscope which had not been visible to the eye previously in the suspension. An oil rich dispersion also became evident but remained fairly uniform in the aqueous suspension. Initial evaluation of the stability of the suspension indicates that IV infusion can be accomplished safely within 1 hour following dilution of the DIM Premix formulation.

Example 5

NET accumulation in acute ischemic stroke (AIS) thromboses is associated with resistance to beneficial activity from tPA and less successful thrombectomy during endovascular therapy (EVT) (Pena-Martinez C, et al., supra, and Novotny J, et al., supra). Evidence of inhibition of NET formation using human neutrophils exposed to DIM therefore demonstrates the mechanism of action for an adjunctive drug therapy to facilitate mechanical thrombectomy (MT) during EVT. Knowing that DIM concentrates in brain tissue following oral administration (see, e.g., Anderton et al. DMD, 32:632-638 (2004)), DIM was evaluated in human neutrophils using established in vitro NET evaluation methods to determine any suppressive activity for cell membrane receptor triggered NET initiation that is relevant to the immunothrombotic process involved in large vessel occluding thromboses.

Methods

Neutrophil isolation: Neutrophils were isolated from the peripheral blood of healthy donors, under a protocol approved by an institutional ethics committee. All subjects gave written informed consent in accordance with the Declaration of Helsinki. Briefly, whole blood was collected using an anticoagulant (sodium citrate), and isolated as previously described using a Percoll gradient separation of neutrophils from other leukocytes (Modulation of multiple neutrophil functions by preparative methods or trace concentrations of bacterial lipopolysaccharide. Haslett C, et al. Am J Pathol. 1985 April; 119(1):101-10). Neutrophils were suspended in RPMI, 2% heat-inactivated human plasma, and 10 mM HEPES, pH7.5 (complete RPMI) to a neutrophil specific concentration of $2.2 \times 10^6$ neutrophils/ml.

Figure 3A:
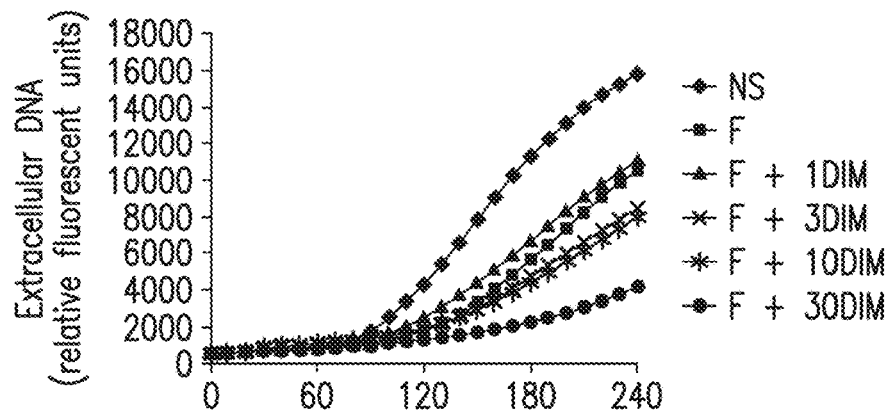
FIGS. 3A-3C show extracellular DNA release in the presence of F Protein and free DIM in DMSO.
Figure 3B:
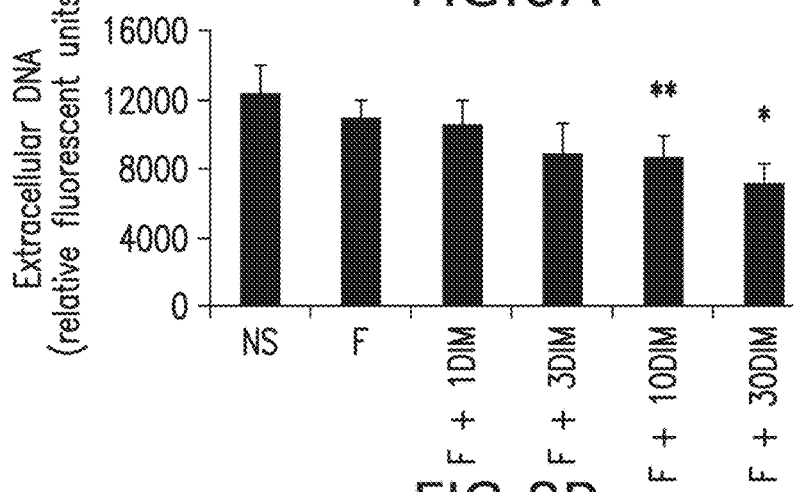

First Neutrophil Extracellular Trap (NET) indicating assay: A Sytox Orange extracellular DNA release assay was utilized. For the experiments using DIM from self-emulsifying SMEDDS BR-9001 (i.e., Example 1), purified human neutrophils ($2 \times 10^5$ per sample) in complete RPMI were allowed to settle in 24-well plates in the presence of DIM from self-emulsifying DIM formulation SMEDDS—BR-9001 (12% DIM) providing experimental DIM concentrations of 1, 3, 10, and 30 µM. Control wells received SMEDDS excipient vehicle mixture alone (diluted to provide excipient mixture concentrations equivalent to excipients present in the 3 and 30 µM DIM experimental wells). Neutrophils ($2 \times 10^5$ per well) were plated in a black-walled 96-well plate and allowed to settle in the presence of DIM from BR-9001 or excipient vehicle control for 30 min. After 30 minutes neutrophils in wells were stimulated with recombinant fusion protein (F Protein (1 µg/ml, Sino Biologicals) or phenolextracted lipopolysaccharide (LPS; 10 µg/ml; List Biologicals).and 5 µM Sytox Orange (Thermo Fisher) was added and gently mixed. The plate was placed in a prewarmed (37° C.) fluorescence plate reader (BioTek FLX-800) and fluorescence read at excitation/emission of 540/600 every 10 minutes over 4 hours. Following this, 1% saponin was added to lyse neutrophils to provide 100% DNA release for experiments presented in FIGS. 1A and 1B. This allowed results to be presented as proportion of total DNA in these experiments. Otherwise results are reported as relative fluorescent units (FIGS. 3A and 3B). The kinetics or 4-hour results were reported as described (See FIGS. 1A and 1B and FIG. 3A).

A second set of experiments were performed using crystalline DIM solubilized in DMSO prior to addition to culture wells. Neutrophils were placed in black-walled 96-well plate as above in the presence or absence of free DIM (1, 3, 10, 30 µM). Free DIM was freshly dissolved in DMSO to 20 mg/ml and diluted 10-fold in complete RPMI. Vehicle controls used DMSO alone diluted similarly to the equivalent concentration of DIM. Neutrophils ($2 \times 10^5$ per well) were plated in the 96-well plate and allowed to settle in the presence of inhibitors for 30 min. As above, cells were stimulated with F Protein, LPS, and 5 µM Sytox Orange was added and gently mixed. The plate was placed in a prewarmed (37° C.) fluorescence plate reader and fluorescence read as above every 10 minutes over 4 hours. Results are reported as relative fluorescent units. The kinetics or 4-hour results were reported as described (See FIGS. 3A and 3B).

Second Neutrophil Extracellular Trap (NET) indicating assay: A micrococcal nuclease (MNase) DNA release assay was utilized to detect extracellular DNA associated with NET formation. The assay was performed as previously described (Neutrophil extracellular trap (NET)-mediated killing of *Pseudomonas aeruginosa*: evidence of acquired resistance within the CF airway, independent of CFTR. Young R L, et al. PLoS One. 2011; 6(9):e23637). Purified human neutrophils ($2 \times 10^5$ per sample) in complete RPMI were allowed to settle in 24-well plates in the presence of DIM from self-emulsifying DIM formulation SMEDDS—BR-9001 (Example 1, 12% DIM) providing experimental DIM concentrations of 1, 3, 10, and 30 µM. Control wells received SMEDDS excipient vehicle mixture alone (diluted to provide excipient mixture concentrations equivalent to excipients present in the 3 and 30 µM DIM experimental wells). After 30 minutes, neutrophils in wells were stimulated with recombinant fusion protein (F Protein (1 µg/ml, Sino Biologicals) or phenolextracted lipopolysaccharide (LPS; 10 µg/ml; List Biologicals). At 4 hours, limited nuclease digestion was performed with micrococcal nuclease (0.5 units/ml; EMB) for 10 minutes at 37° C. to release extracellular DNA fragments. Nuclease activity was then stopped with 5 mM EDTA, and cellular debris was removed by centrifugation. DNA content was measured with the Quant-iT™ Picogreen assay (Invitrogen) with a standard curve ranging from 10 to 1000 ng DNA/mL used to calculate DNA release in samples (See FIGS. 1C and 1D).

Fluorescent imaging of extracellular DNA for photomicrograph data: Neutrophils ($5 \times 10^5$ per well) were spotted on a glass microscope chamber slide (Ibidi) and cells were stimulated for 4 hours as indicated above with F Protein or LPS, at 37° C. in a humidified chamber, and stained with 0.2 µM Sytox Orange for the final 10 minutes. The slides were fixed in 2% formaldehyde (Sigma) for 10 min at room temperature and imaged. Microscopy was performed with a Zeiss Axiovert 200M. Representative photo images are presented in FIG. 2 and FIG. 3C.

Figure 1B:
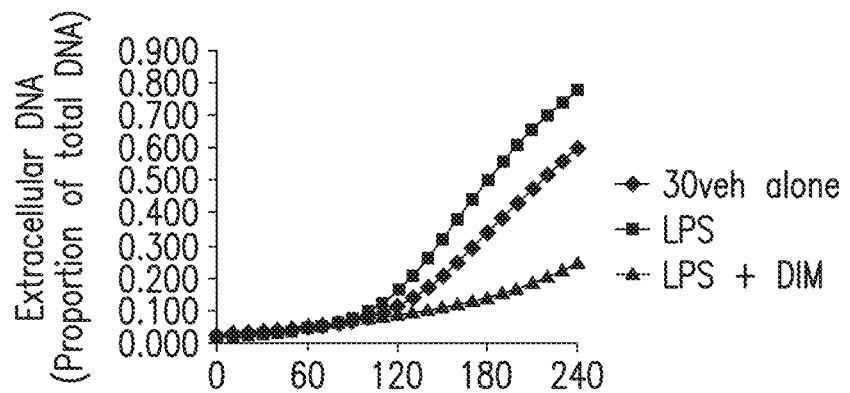

Results: Human neutrophils stimulated with both F Protein and LPS using fluorescence of the cell-impermeable double-stranded DNA-binding dye Sytox showed a clear dose dependent inhibition of extracellular DNA over 4 hrs of timed sampling. Using DIM from BR-9001 (Example 1), dose responsive inhibition was shown from 1 µM through 30 µM (FIG. 1A). DIM from BR-9001 clearly reduced DNA release over 4 hours in neutrophils stimulated with LPS (FIG. 1B). DNA release in the presence of DIM resulted in a delay in DNA release of about 1 hours from that in the absence of DIM, indicating more quiescent neutrophils despite contact with receptor specific stimulators (F protein and LPS). This activity was confirmed for free DIM without self-emulsifying excipients. As observed with DIM from BR-9001, free DIM had a dose-dependent inhibitory effect on DNA release as measured by Sytox Orange assay (FIGS. 3A and 3B).

Figure 1C:
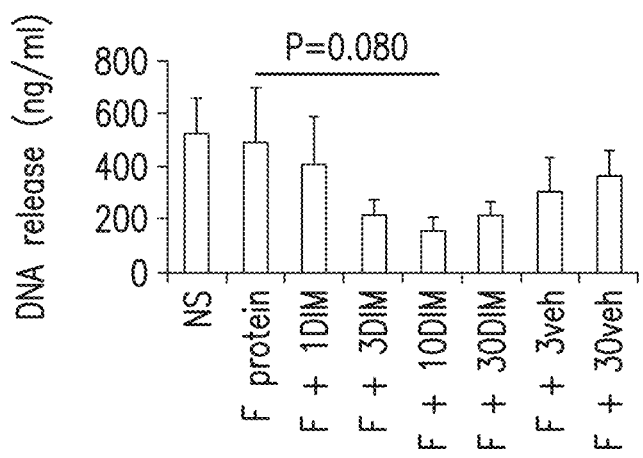
Figure 1D:
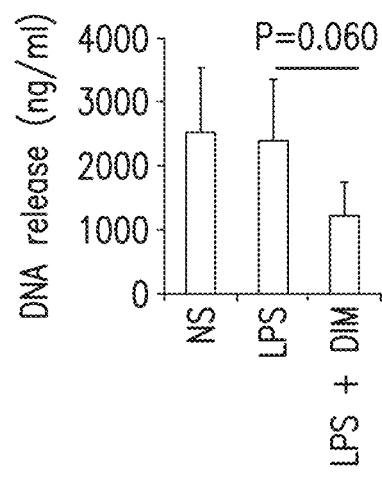

Confirmation of the NET formation inhibitory activity of DIM was obtained by measuring release of NET specific extracellular DNA fragments by using a micrococcal nuclease (MNase) DNA release assay. A clear inhibitory effect of DIM from BR-9001 on extracellular DNA release was observed (FIGS. 1C and 1D). In this case BR-9001 showed dose-dependent inhibition of MNase-released DNA fragments in the presence of F Protein using BR-9001 from 1 to 30 µM (FIG. 1C) and BR-9001 (30 µM) inhibited DNA fragment detection in the presence of LPS (FIG. 1D).

Figure 2:
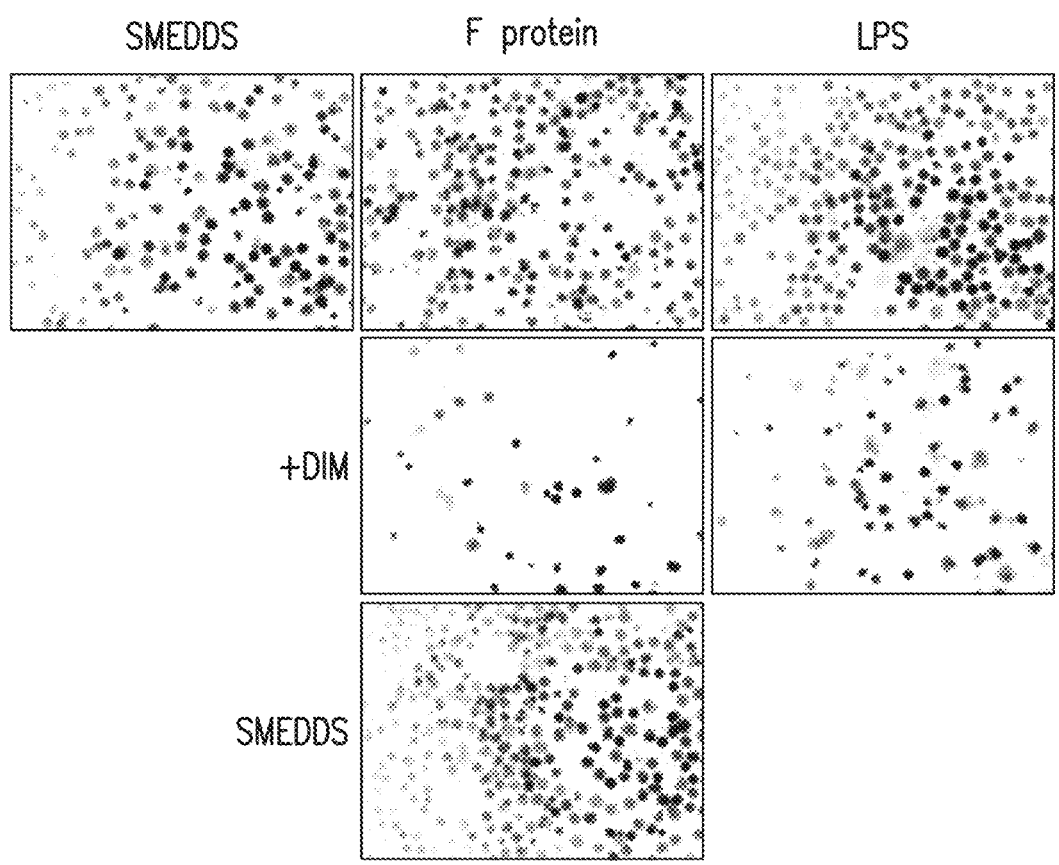
FIG. 2 shows visualization of extracellular DNA by cell-impermeable Sytox Orange in the presence of DIM (30 Neutrophils were treated with F Protein (1 µg/mL), LPS (10 µg/mL) and SMEDDS DIM or SMEDDS vehicle excipients alone in the absence of DIM for 4 h. Data is representative of 2 independent experiments.
Figure 3C:
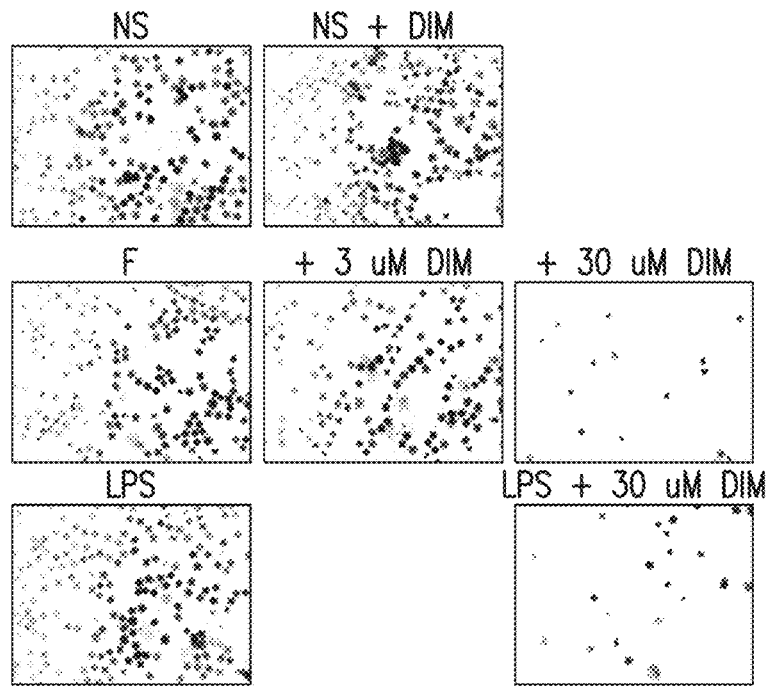

Further confirmation of the inhibition of NET formation and propagation was obtained using fluorescence microscopy. Extracellular DNA in the presence of Sytox Orange was visualized by using standardized fluorescence microscopy methods. Fewer neutrophils releasing extracellular DNA after treatment with F Protein or LPS were apparent in the presence of DIM from BR-9001 (FIG. 2). The BR-9001 SMEDDS vehicle excipient had no effect on extracellular DNA in the presence of F Protein, identifying DIM as the active agent (FIG. 2). Additional experiments visualized inhibitory activity of API DIM on NET formation with self-emulsifying excipients. Following exposure to DIM, absence of extracellular DNA in the presence of F Protein and LPS was observed directly by fluorescent microscopy of Sytox Orange. DIM inhibited visualization of extracellular DNA by both F Protein and LPS (FIG. 3C). A dose response for extracellular DNA positive cells was seem from 3 µM to 30 µM DIM. DIM did not inhibit spontaneous DNA release in non-stimulated neutrophils.

Discussion: Taken as a whole, the experiments indicate that DIM inhibits NET formation and NET propagation, or "NETosis", over time as reflected by NET specific DNA release assays. DIM inhibited the neutrophil NET response in the presence of the receptor dependent stimulators F Protein and LPS. The observation that DIM did not appear to affect DNA release in non-stimulated neutrophils suggests that DIM acts on intracellular signaling events that are independent of spontaneous DNA release observed in these studies. The inhibition of DNA release in the presence of F Protein was dose-dependent. The estimated $IC_{50}$ of between 1 and 3 µM for DIM from BR-9001 is clinically relevant as these plasma concentrations are seen in humans using BR-9001 and related prototype self-emulsifying formulations following an oral dose of 300 mg DIM (See, e.g., U.S. Pat. Nos. 9,928,965 and 10,441,569; and U.S. Patent Publication No. 2018/0280347). The lower estimated $IC_{50}$ between 3 and 30 µM for free DIM is consistent with the known low solubility of crystalline DIM as an API in aqueous media.

It is important to note that the results were confirmed using three independent methods of detecting DNA release: limited digestion, isolation, and measurement of extracellular DNA fragments by the MNase assay; kinetic detection of extracellular DNA using the cell-impermeable fluorescent DNA dye Sytox Orange; and the direct observation of extracellular DNA by fluorescence microscopy using Sytox Orange. This data predicts clinical efficacy to reduce NET formation and NETosis in the setting of LVO using both oral BR-9001 and intravenous DIM.

Example 6

In Vitro Screening Method for Evaluation NET Suppressive activity of DIM-Second Active Agent Combinations Introduction: Combined administration of NET suppressive 3,3'-diindolylmethane (DIM) with second active agents is indicated as a rational approach to improving the efficacy of DIM alone in treatment of NET-related thrombosis before and after EVT with MT. In vitro screening utilizing neutrophils activated by serum isolated from severe COVID-19 patients is summarized below as a pre-clinical test system to screen promising DIM-second active agent combinations. This screening method makes use of established Sytox Orange NET visualization technology combined with the finding that serum from actively infected COVID-19 patients provides a potent and consistently active, in vitro activator for cultured neutrophils (Zuo et al. JCI Insight 2020 Apr. 24; 138999. doi: 10.1172/jci.insight.138999).

In Vitro Test System Overview:
1. Unstimulated neutrophils are obtained and isolated from a healthy donor.
2. Activation serum is obtained from a patient with active and severe COVID-19 disease.
3. Placebo SMEDDS vehicle is obtained for uniform dissolution of DIM and test second active agent.
4. DIM alone is dissolved in Placebo SMEDDS vehicle.
5. Second active agent alone is dissolved in Placebo SMEDDS vehicle.
6. DIM and second active agent are dissolved together in placebo SMEDDS vehicle to provide DIM at 5 µM and second active agent at 5-20 µM final concentrations in neutrophil culture media.
7. Donor neutrophils are stimulated with activation serum alone for 4 hours.
8. Donor neutrophils are stimulated with activation serum plus DIM for 4 hours.
9. Donor neutrophils are stimulated with activation serum plus second active agent for 4 hours.
10. Donor neutrophils are stimulated with activation serum plus DIM and second active agent for 4 hours.
11. All culture conditions are assayed for NETosis activity using the Sytox Green assay method.
12. Florescence is quantified for each above condition at wavelengths of 504 nm and 523 nm.
13. Suppression of NETosis by DIM in combination with the second active agent is compared to suppression of NETosis by DIM and second active agent alone.
14. Second active agents which do not inhibit DIM suppression of NETosis or provide additive suppression of NETosis with DIM are advanced to in vivo anti-COVID-19 evaluation.

Examples of DIM-Second Active Agent Combinations for Testing in COVID-19 Activated Neutrophil Culture

| Diindolylmethane (DIM) Component | Second Active Agent Component |
| --- | --- |
| DIM | Ticagrelor |
| DIM | Ebselen (PZ 51, DR3305, SPI-1005) |
| DIM | Fingolimod (FTY720) |
| DIM | Anakinra |
| DIM | Dimethyl Fumarate (Tecfidera) |

Details of Methods for Needed Neutrophil Culture and Standard Sytox Orange Assay Technique Human neutrophil isolation: For neutrophil preparation, blood from healthy volunteers is collected into sodium citrate tubes by standard phlebotomy techniques. The anti-coagulated blood is then fractionated by density-gradient centrifugation using Ficoll-Paque Plus (GE Healthcare). Neutrophils are further purified by dextran sedimentation of the red blood cell layer, before lysing residual red blood cells with 0.2% sodium chloride. Neutrophil preparations are at least 95% pure as confirmed by nuclear morphology before using in NETosis assay.

Standard NETosis assay using SYTOX Green: A cell-impermeant dye SYTOX Green (Thermo Fisher) is used to measure NETosis. Purified donor neutrophils are resuspended in 1×PBS (Gibco). 1×105 neutrophils are seeded into each well of a 0.001% poly-L-lysine-coated 96-well black clear-bottom non-tissue culture plate, and are allowed to adhere for 20 minutes at 37° C. and 5% CO2. PBS is gently removed and Patient Activation serum (diluted to 10% in RPMI culture media supplemented with L-glutamine) is added without disrupting adherent cells. SYTOX Green is added at the same time to a final concentration of 500 nM. All treatments are done in triplicate. Cells are allowed to undergo NETosis for 4 hours. Culture media is then gently removed and fresh 1×PBS is added to each well. Fluorescence is quantified at excitation and emission wavelengths of 504 nm and 523 nm for each culture condition, using a Cytation 5 Cell Imaging Multi-Mode Reader (BioTek). Data are collected using the area-scan setting of the plate reader. Influence of DIM alone, DIM plus second active agent, and second active agent alone on relative fluorescent units is compared and analyzed.

Example 7

Co-Formulated Oral SMEDDS Compositions Containing DIM and a Second Active Agent

In one embodiment, provided herein are compositions comprising a second active agent in addition to DIM. Requirements for selection of a compatible second active agent include physicochemical compatibility of the second active agent including predominant lipid solubility, acceptable solubility in the DIM-specific solvent, surfactant, and co-surfactant components (e.g., SMEDDS), and low dose loading requirements to allow co-solubilization with DIM in the SMEDDS. Favorable complimentary second active agents do not interfere with or enhance bioavailability of DIM following spontaneous emulsification of compositions described herein, and, optionally, inhibit recrystallization of DIM and/or do not recrystallize during digestion. The most favorable second active agents that can be used in the compositions described herein are lipid soluble drugs with Log P greater than 1.5. Co-formulation with DIM in SMEDDS excipients provides a combined composition which increases oral bioavailability of both DIM and the co-formulated second active agent. In one embodiment, co-formulated second active agents include all-trans retinoic acid and chloroquine.

Co-Formulation of Complementary Anti-NET Compounds with DIM

| Name of complementary anti-NET Second Active Agent (API) | Trade Name of Second Active Agent | Log P of Second Active Agent | Dose Range of Second Active Agent per capsule (mg) | DIM Dose Range per capsule (mg) | Daily Dose of DIM and Second Active Agent in number of capsules |
|---|---|---|---|---|---|
| All trans retinoic acid | Tretinoin | 6.83 | 2-10 | 50-100 | 2-4 Three Times per Day |
| chloroquine | Chloroquine | 4.69 | 50-100 | 50-100 | 2-3 Three Times per Day |
| Ticagrelor | Brilinta | 1.90 | 60-90 | 50-100 | 2-3 Three Times per Day |
| Fingolimod (FTY720) | Gilenya | 5.25 | 0.25-0.5 mg | 100-125 | 2-3 Three Times per Day |

Manufacture of SMEDDS Co-Formulations with Compatible Second Active Agents

The following were added to a small scintillation vial in the following order: 2.8 grams caprylocaproyl polyoxyl-8 glycerides (LABRASOL® ALF), 1.8 grams lauroyl polyoxyl 32 glycerides (GELUCIRE® 44/14), 2.4 grams poloxamer 124, 1.0 grams oleoyl polyoxyl-6 glycerides (LABRAFIL® M1944CS). The mixture was warmed and gently agitated to uniformity. 0.8 Grams of phosphatidyl choline (Lipoid PHOSPHOLIPON® 90G) was added to the mixture with warming to approximately 70° C. Maintaining the warmed temperature, 0.25-150 mg of second active agent is added with continued mixing. After cooling to approximately 50° C., 0.6-1.2 grams of 3,3'-diindolylmethane is added with continuing agitation until the mixture is uniform.

Example 8

DIM Inhibits NETs in an Animal Model Relevant to Acute Ischemic Stroke (AIS)

Ferric chloride, applied topically and directly to the middle cerebral artery of an anesthetized mouse, has been shown to trigger accumulation of neutrophils and NETs in amounts closely resembling the makeup of human thromboses obtained during EVT (Novotny J, et al. Histological comparison of arterial thrombi in mice and men and the influence of Cl-amidine on thrombus formation, PLoS One, 2018 Jan. 2; 13(1):e0190728. doi: 10.1371). Adapting established methods for the application of ferric chloride and following neutrophil and NET accumulation in anterior cerebral artery thrombosis, provides a model in which the NET inhibitory activity of DIM can be demonstrated. Using methods adapted from Novotny J, et al. (supra), histological comparison of arterial thrombi in mice on thrombus formation, pre-clinical studies are performed which demonstrate the activity of DIM administered orally and intravenously to inhibit neutrophil and NET accumulation in cerebral arteries relevant to AIS in humans.

Methods:

Pathogen-free mice with C57BL6/J background are obtained from Charles River. All mice to be used for experiments will between 8 and 14 weeks old and weigh between 25 and 35 g. Each experimental group is weight- and sex-matched so that experiments are carried out on male and female mice with similar weight and in equal distribution between groups. All procedures are performed on anaesthetized animals. Animals are sacrificed under deep anesthesia. For thrombus induction in the carotid artery in vivo, local application of $FeCl_3$ was made. Mice are anesthetized using 2% isoflurane and intraperitoneal injection of fentanyl (0.05 mg/kg), midazolam (5.0 mg/kg) and medetomidine (0.5 mg/kg). Thereafter, the common carotid artery was exposed. To induce arterial thrombosis, a filter paper (0.5±1.0 mm) saturated with 10% $FeCl_3$ is applied for 3 minutes at the lateral side of the carotid artery adventitial surface (close to the carotid bifurcation) as described previously (Fay W P, et al. Vitronectin inhibits the thrombotic response to arterial injury in mice, Blood, 1999; 93(6):1825-30). To investigate leukocyte accumulation over time, thrombus growth was allowed for up to six hours before the vessels are excised. Murine carotid arteries are harvested and rinsed with PBS, embedded in O.C.T. compound and frozen at −80° C. Both human thrombi and murine vessels were cut into 5 μm thick sections using a cryotome. Specimens were fixed in 4% formaldehyde solution for 4 min, washed in PBS, and blocked with serum or 5 μg/ml anti-mouse CD16/32 (eBioscience) and 1% BSA (PAA Laboratories) in PBS for 30 min. Sections were incubated with primary antibodies (Table) for one hour at room temperature, and are then washed in PBS+0.1% Tween. Detection is performed with fluorescent secondary antibodies listed as follows:

List of Antibodies Used for Immunohistochemistry

| Antigen | Primary Antibody | Clone | Secondary Antibody |
|---------|------------------|-------|--------------------|
| CD45 | Rat | 30-F11 | Donkey anti-rat Alexa Fluor 488 |
| NE | Rabbit | Ab68672 | Goat anti-rat Alexa Fluor 555 |
| Histone H3 | Rabbit | Citruline R2 + R8 + R17 | Goat anti-rabbitAlexa Fluor488 |

Experimental Groups for Study:
1. Oral DIM from BR-9001, dosed before anesthesia and application of Ferric Chloride (FeCl$_3$) to carotid/cerebral artery. n=3-5, males and females—peroral experimental group.
2. Oral Placebo excipient mixture for BR-9001, dosed before anesthesia and application of FeCl$_3$ to carotid/cerebral artery. n=3-5, males and females (positive control group).
3. Intravenous DIM suspension (Example 4), dosed at the time of FeCl$_3$ application to carotid/cerebral artery. n=3-5, males and females—intravenous experimental group.
4. Intravenous DIM suspension (Example 4), dosed at 1 hour past the time of FeCl$_3$ application to carotid/cerebral artery. n=3-5, males and female—intravenous clinical treatment group.

Following histologic preparation, leukocytes are identified by expression of CD45, neutrophils are identified by expression of neutrophil elastase (NE), and Histone H3 antibody is used to visualize histones which are specific for NET formation. All immunofluorescence images, including controls, are optionally stained with a nuclear dye (DAPI or Hoechst, as indicated)

Analysis of Histology and Microscopy for Immunofluorescent Staining.

Images are acquired using either a Zeiss Imager M2 Axio epifluorescence microscope, or a Leica DMRB epifluorescence microscope with a Zeiss AxioCam and processed with an AxioVision software (Zeiss). Neutrophils and NETs are counted in four fields of view using a 40× objective (176× 131 µm). The results are extrapolated to cells/mm2 or NETs/100 leukocytes. In these experiments, the NETs in thrombosis sample are identified:1) presence of filamentary structured extracellular DNA, 2) respective filamentary structures that are decorated with a marker for neutrophil granule proteins (like NE) or citrullinated histone H3.

To determine differences between groups, data are analyzed using a two-tailed unpaired StudentÁs t-test or one-way ANOVA for multiple comparisons. A value of $P<0.05$ is considered significant.

Anticipated Results:

Regarding presence and accumulation of NETs in arterial thrombi of mice, DIM treatment is expected to abrogate NET formation and diminished the number of neutrophils in arterial thromb compared to control treatment. Both oral and intravenous administration groups (Groups 1,3,4) show lower numbers of NETs compared to positive control (Group 2) as demonstrated by immunostochemistry staining and counting in thrombosis samples. Since neutrophils can exhibit strong pro-coagulatory properties by releasing NETs, the inhibition of neutrophil and NET counts in thrombi from mice provide evidence of efficacy relevant to treatment of AIS and treatment using DIM with EVT and MT in patients. The established similarities between ferric chloride induced thrombosis in mice and human thromboses (Novotny J, et al., 2018, supra), make the NET inhibitory effects of DIM in mice relevant and predictive of similar NET inhibition in human thromboses. It is expected that other, similar IV DIM formulations, e.g., Formulation #8, Example 11, will provide similar results.

Example 9

Prototype Placebo-Controlled Clinical Trial Design for Use of DIM (BR-9001) in AIS Patients aged between 18 and 85 with anterior circulation AIS who are not eligible for alteplase (tPA) and are candidates for mechanical thrombectomy (MT) commenced within 9 hours of stroke onset will be enrolled if they present with an infarct core volume between 15-100 mL with at least 20% mismatch (as evaluated by CTP) and intracranial occlusion in proximal cerebral arteries. Inclusion criteria are standard contraindications to alteplase; Exclusion criteria are (1) evidence of other diseases of the CNS; (2) pre-existing neurologic disability (a score greater than 2 on the modified Rankin Score (mRS)); (3) swallowing difficulties that would prevent administration of oral BR-9001; (4) patients with any history of bradyarrythmia, atrioventricular block or current use of beta-blockers or verapamil; (5) concomitant use of antineoplastic, immunosuppressive or immune modulating therapies; (6) macular edema.

Intervention: Patients will be randomized to either ME with pre and post procedure Active (DIM, BR-9001, Example 1) or ME with pre and post procedure Placebo (Excipient Only).

Patients randomized to BR-9001 will receive oral BR-9001 100 mg liquid filled capsules at a dosage of 300-400 mg DIM three times daily, for three consecutive days, with the first dose being given at the time in which patients are enrolled which is about one hour prior to mechanical thrombectomy (MT).

Patients randomized to Placebo Excipients will receive visually matched Placebo Excipient capsules with color-matched equivalent excipients only three times daily, for three consecutive days, with the first dose being given at the time in which patients are enrolled which is about one hour prior to mechanical thrombectomy.

Blood will be sampled on Days 2 and 3 and assayed for cell free DNA. Patients will receive all other standard post stroke in hospital care. Patients will be re-assessed after 90 days post stroke as to their Rankin Score.

Example 10

Summary of Drug Product Development Steps for Oral SMEDDS DIM (BR-9001) in Conjunction with Endovascular Therapy (EVT) and Mechanical Thrombectomy (MT) for Acute Ischemic Stroke (AIS) Intervention.

| | |
|---|---|
| Patient Population | Adults immediately following Acute Ischemic Stroke (AIS) |
| Estimate of the burden of AIS on the US healthcare system | ~690,000 yearly AIS cases in USA, growing by at least 2% per year based on projected growth of over 65 "Senior" population |
| Clarity of Regulatory Path | Clear, in that EVT with MT with and without tPa therapy for AIS is under active evaluation in clinical trials. Phase II Clinical Trials would add BR-9001 (Active) (Example 1) and BR-9001 Excipients Only (Placebo) (Example 1) arms to existing protocols for AIS patients undergoing EVA Thrombectomy without tPa. |
| Size, Duration and complexity of Clinical Trials | Phase II Clinical Trials will require careful inclusion criteria, require ~60-100 screened patients (15-25 in each of 4 groups) There are standard outcome measures at 90 days past stroke intervention including the Rankin Score. Phase III trials will require group sizes of 100 or more. |
| Ability to identify and recruit patients | Hospital setting and established imaging screening protocols will facilitate enrollment. If Phase 1 safety study shows BR-9001 to be safe at the study dose in healthy elderly. BR-9001 will proceed to Phase II trials and facilitated recruitment will be driven by high physician motivation to improve AIS EVT and MT outcomes. |
| Burden of proof required for Market Access | Any 90-day outcome Improvement linked to DIM administration which is statistically significant compared to current standard of care without DIM, will motivate regulators to allow market access. |
| Pre-clinical Support Needed and Clinical Trials to Follow | A well designed, pre-clinical efficacy study with BR-9001 in an established animal model of AIS is needed. Path to Market will require Phase 1 dose optimization in elderly subjects and placebo-controlled Phase II efficacy clinical trials. |

Example 11

Development and Use of an Optimized, Parenteral, DIM Premix Drug Product

Introduction: Increased accumulation of Neutrophils and Neutrophil Extracellular Traps (NETs) following thrombosis onset in both Acute Ischemic Stroke (AIS) and Acute Coronary Syndrome (ACS) contributes to poor clinical outcome following Endovascular Therapy (EVT) (Novotny J, et al. Thrombus NET content is associated with clinical outcome in stroke and myocardial infarction. Neurology. 2020 Jun. 2; 94(22):e2346-e2360.). The efficacy of EVT and thrombectomy in AIS and ACS sharply decreases with greater time past symptom onset. Because EVT for AIS and ACS is restricted to comprehensive stroke and cardiac centers, time-consuming transport of patients is often required. Similarly, extensive imaging procedures needed to categorize and localize the anterior or posterior cerebral vessel thrombosis in AIS may delay the start of EVT. New treatments which increase the time window for initiation of EVT providing for improved outcomes are needed. The following describes the development of a concentrated, premix IV drug product which provides shelf stable DIM. The drug product is ready for dilution into a nano-scale suspension and for immediate intravenous administration by pre-hospital Emergency Medical Technicians (EMT's), by in-hospital Emergency Departments, and by Interventional Radiologists. Such a drug product advances current protocols for use during pre-hospital and inter-hospital transport, as well as pre-EVT and during EVT treatment in critically ill patients. A drug formulation yielding a dispersion of nano-scale particles of DIM for intravenous and/or intra-arterial use fills an important unmet need to arrest thrombosis progression, limit neutrophil and NET accumulation in ischemic tissue and improve the outcome of EVT for both AIS and ACS.

The extremely low solubility of DIM in both oil and water combined with regulatory restrictions on the number of acceptable excipients for parenteral administration make development of a functional premix for API DIM a formidable formulation challenge. Safety concerns related to parenteral administration of lipid-based excipients, surfactants and polymers put limitations on formulation development for a DIM-related parenteral premix. Working within these constraints, DIM compatible excipients with appropriate solubilizing activity and safety record were determined based on physicochemical characteristics and history of prior regulatory approval (Table 1). These formulation excipient components are clearly different than those discovered to provide Self Micro-Emulsify Drug Delivery (SMEDD) formulations for oral administration of DIM-related indoles as specified in U.S. Pat. Nos. 9,918,965, 10,441,569, and 10,779,479). The present premix formulations were assessed for ability to dissolve DIM or DIM derivatives. Following this, the premix formulations were tested for dispersion formation following dilution in physiologic aqueous media to emulate clinical use. Formulations 1-10 were observed following spontaneous dispersion formation and the stability of the resulting nano-scale dispersions was assessed. The interactive excipient mixtures were also evaluated following dispersion in standard heparinized saline to emulate use as a catheter flush product for both venous and arterial administration during EVT and thrombectomy for AIS and ACS.

TABLE 1

Excipient Materials Selected as Candidates for Parenteral DIM Formulations

| Excipient | Tradename | Manufacturer | Physical Form |
|---|---|---|---|
| Diethylene glycol mono-ethyl ether | Transcutol | Gattefosse | Liquid |
| Medium chain triglycerides | Labrafac WL1349 | Gattefosse | Liquid |
| Oleoyl polyoxyl-6 glycerides | Gattefosse Labrafil M1944CS | Gattefosse | Liquid |
| Phosphatidyl choline | PHOSPHOLIPON ® 90G | Lipoid | Solid |

TABLE 1-continued

Excipient Materials Selected as Candidates for Parenteral DIM Formulations

| Excipient | Tradename | Manufacturer | Physical Form |
|---|---|---|---|
| Polyoxyl-15 hydroxystearate | Kolliphor HS-15 | BASF | Semi-solid |
| Pol oxamer 188 | Kolliphor P188 | BASF | Solid |
| Poloxamer 407 | Kolliphor P407 | BASF | Solid |
| Diindolylmethane (DIM) | Pharmaceutical DIM | BioResponse | Crystalline Solid |
| 95% Ethanol | Everclear | Sigma Aldrich | Liquid |
| Sodium chloride | | Sigma Aldrich | Solid |

Manufacture of Anhydrous DIM Premix Formulations

The following premix prototypes were prepared at a quantity of 10 grams each (Table 2). Transcutol (Gattefosse, FR) was included as a candidate excipient although it is not currently used in approved parenteral products. Transcutol has been tested in Europe for parenteral use and considered to be safe for potential use in IV formulations. Likewise, toxicity studies in animals have shown that M1944 CS (Gattefosse, FR) is well tolerated and could have potential for inclusion in parenteral formulations. The other excipients are currently used in approved parenteral formulations.

TABLE 2

Composition of Candidate Undiluted Premix Parenteral DIM Formulations
Ingredients Specified as Percentages of Contained in the Formulation

| | Formulation # Excipient Ingredient | | | | | | | | | |
|---|---|---|---|---|---|---|---|---|---|---|
| | 1 | 2 | 3 | 4 | 5 | 6 | 7 | 8 | 9 | 10 |
| Ethanol | 65 | 62 | 42 | 39 | 49 | 59 | 40 | 45 | 30 | 49 |
| Gattefosse Transcutol | | | | 10 | | | 13 | | 15 | 17 |
| Gattefosse WL 1349 | 6 | 4 | 4 | | | 9 | 16 | 10 | 10 | 12 |
| Gattefosse M1944CS | | | | 10 | 9 | | | | | |
| Phosphatidyl Choline | 7 | 7 | 7 | 7 | 8 | 8 | 8 | 8 | 8 | |
| BASF HS-15 | | 5 | 5 | 12 | 10 | | 21 | 15 | 15 | 17 |
| Poloxamer 188 (Vepoloxamer P-188) | 6 | 6 | 12 | 8 | 10 | 11 | | 8 | 8 | 8 |
| Poloxamer 407 | 14 | 14 | 28 | 12 | 12 | 11 | | 12 | 12 | 12 |
| Diindolylmethane | 2 | 2 | 2 | 2 | 2 | 2 | 2 | 2 | 2 | 2 |

Method of Manufacture and Preliminary Evaluation of Undiluted DIM Premix Formulations The ten candidate formulations were prepared by adding each of the ingredients to the ethanol with stirring. After the final ingredient, the mixture was stirred to uniformity for 10 minutes using a magnetic spin bar. The product mixture was examined for clarity and fluidity after 2 hours at room temperature. Observations included the following: Formulation #1, #2, #6, #7, #8—all produced clear solutions, Sample #4 contained some suspended solids, Samples #5 and #10 were opaque. Samples #3 and #9 were semi-solid. From these observations it was concluded that some amount of medium chain triglyceride and/or phosphatidyl choline is needed to accomplish complete dissolution of API DIM; larger amounts of ethanol are needed relative to the poloxamers to prevent gelation of the premix, and Transcutol does not function to prevent gelation. Based on the observations Formulations #3, #5, #9, and #10 were considered poor candidates for further development.

Dispersion Testing of Candidate Premix Formulations

Each of the formulations were dispersed in 0.9% saline by pipetting 1 mL of the candidate solution into 8 mL of saline. The pipette was rinsed with 1 mL of saline and the suspension was shaken vigorously by hand for 5 minutes. The semi-solid formulations were warmed slightly in a water bath to become fluid prior to dispersion in saline solution. The uniform suspensions produced all contained 20 mg DIM per mL. Each suspension was examined by light microscopy for any visible particulates. The microscope slides were immediately examined after preparation and then again at 2 hour and 4 hour time intervals following dispersion and without further mixing. Additionally, a prototype premix using the #8 formulation was prepared but this time including DIM with additional all trans retinoic acid (ATRA) added at half the concentration of the DIM. The dissolution of both DIM and ATRA indicated reserve excipient capacity to accommodate a lipophilic second active API in the #8 formulation. This combined formulation was tested similarly to the other samples for dispersion. Other appropriate second active APIs for addition to Formulation #8 and co-administration with DIM include 1, 1-bis(3,3'-indolyl) ethane ("HB-237"), EP-7041 (eXlthera Pharmaceuticals), and LPN023 (Novartis).

Observations following dispersion of candidate DIM Premix formulations in saline:

1 2-5 micron particles evident, some spherical drops and irregular shapes, no crystals at 2, 4 hours

2 some texture noted, some irregular shapes, looks fairly clean, no crystals at 2, 4 hours

3 dispersion a bit foamy, some small particles, no crystals at 1, 2, or 4 hours

4 very few particles, a little texture, no crystals at 2, 4 hours

5 some large globules, 1 to 2 micron particles evident, texture in background, no crystals at 2, 4 hrs

6 many 2-3 micron shapes, worst seen so far, a few crystals starting to form at 4 hours, none before

7 some larger particulates, small drops in background, contains crystals at 2 to 4 hours

8 very few specs, essentially clear, no spheres or texture, no crystals at 2 or 4 hours

9 a few fine particles and specks, no crystals forming up to 4 hours

10 many drops observed at 2 to 5 microns, drops observed again at 2.5 hours, no crystals forming at up to 4 hours Based on these observations, Sample #8 was chosen for further evaluation. A solution of heparinized saline was prepared at 10 units of heparin per mL of saline. The 1 mL sample of #8 was dispersed similarly in the heparinized saline as before in regular saline. There were no discernible differences in the initial dispersion or its stability with no DIM crystal precipitate discernible when subjected to light microscopic examination. Likewise, when the #8 formulation was prepared with all ATRA at half the concentration of the DIM in combination with the DIM, the dissolution of the ATRA was complete but required a bit more mixing and slight warming of the suspension in a water bath. It should be noted that the ethanol solubility of ATRA is only 5 mg/mL where the proposed formulation was at 10 mg/mL. The excipients seemed to improve the solubility of the ATRA but this should be examined further for stability of the formulation. The dispersion went equally as well as the formulation without ATRA and did not show any yellow crystals of ATRA observable microscopically either initially or after 4 hours.

Evaluation of a Dispersed IV DIM Formulation Using Dynamic Light Scattering Particle Size Analysis Dynamic Light Scattering (DLS) is also known as Photon Correlation Spectroscopy DLS is used to characterize the size of various particles including proteins, polymers, micelles, carbohydrates, and nanoparticles. Solutions of poloxamers generally form micelles and depending on a number of factors such as concentration, temperature and composition. Micelles have particle sizes in the range of 200 nanometers (Almeida, M., Magalhães, M., Veiga, F. et al. Poloxamers, poloxamines and polymeric micelles: Definition, structure and therapeutic applications in cancer. J Polym Res 25, 31 (2018)). Particle size of Poloxamer 407 suspensions have been reported in dilute solution and show a size of approximately 300 nm (Dukhin, A. S., Goetz, P. J. Applications for Emulsions and Other Soft Particles, in Characterization of Liquids, Dispersions, Emulsions, and Porous Materials Using Ultrasound (Third Edition), 2017). In addition to particle size by DLS, The Polydispersity Index (PDI) is a parameter used to define the size range of lipidic nanocarrier Systems. The term "polydispersity" or "dispersity" is used to describe the degree of non-uniformity of the size distribution of particles. In safety and regulatory review of drug delivery applications using lipid-based carriers, a PDI of 0.3 and below is considered to be acceptable and indicates a homogenous population of particles.

Figure 4:
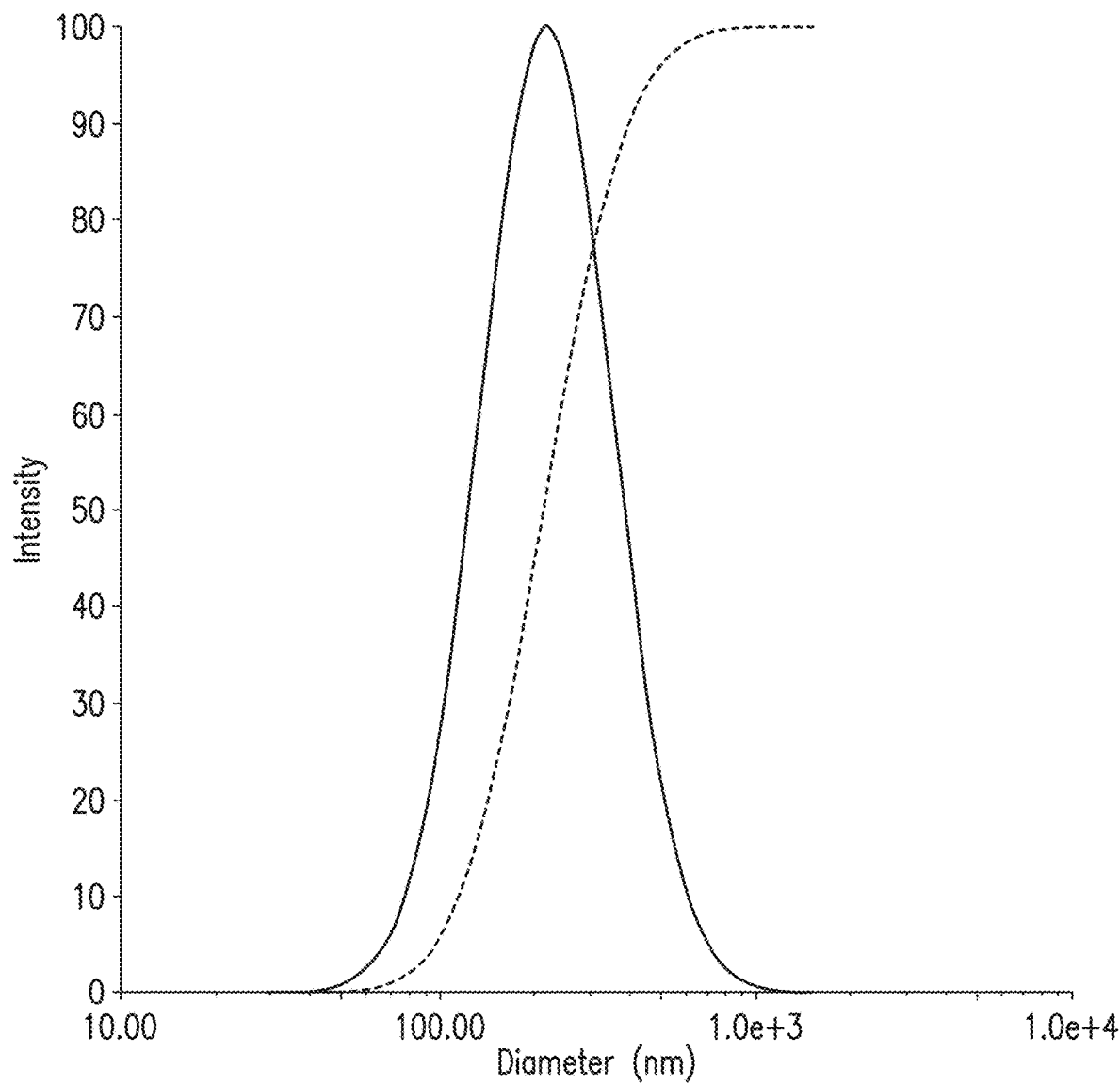
FIG. 4 shows the Dynamic Light Scattering (DLS) Report Graph from the particle size and polydispersity testing following dispersion of 1ml of the Formula #8 premix into 100 ml of physiologic saline. Using a Brookhaven Instrument DLS apparatus, the measurement showed an Effective (Eff) diameter of 218.25 nm and a Polydispersity (PDI) of 0.259.

One Example of the current formulations developed, Sample #8 (See Table 2) was carried forward into Particle Size and PDI evaluation. Sample #8 was diluted 1 mL into 100 mL of standard saline and gently mixed with a magnetic spin bar. The particle size was measured using a Brookhaven Dynamic Light Scattering instrument. The results from showed an Effective (Eff.) Diameter of 218.25 nm. The PDI was determined at 0.259 nm which is under the FDA upper limit guidance of 0.3 for this type of product (see, e.g., FIG. 4).

Conclusions Regarding DIM Premix Formulation and Dispersion Testing

The #8 formulation produced the cleanest dispersion observed using microscopy with no crystals of DIM forming at up to 4 hours. This was true for both saline and heparin/saline dispersions as well as when ATRA was included with DIM as a second active API. These observations were confirmed by subsequent dynamic light scattering measurement of particle size in a standard suspension of 100 ml. It is concluded that the use of the Kolliphor HS-15 and the phosphatidyl choline produce smaller particle size micellar suspensions and the use of the poloxamers improves the clarity of the dispersion and may prevent drug precipitation. There is a minimum amount of ethanol required at 45 to 50% for the candidate drug product to remain fluid and uniform in the premix. The use of Transcutol does not seem to improve the formulation performance allowing crystal formation on dispersion, not seen with formulation #8. In conclusion, Formulation #8 proved to be one of the best of the premix formulations and utilizes previously approved excipients with a history of safe use in parenteral drug products. Formulation #8 consists of a mixture of ethanol, Kolliphor HS-15, Gattefosee WL 1349, phosphatidyl choline, Kolliphor P188, Kolliphor P407, and Diindolylmethane (DIM).

Projected Clinical Use of the DIM Premix Drug Product

The DIM premix formulation is intended for early initiation of DIM-based post stroke and ACS therapy in critically ill patients not able to safely take oral medication. The goal of administration is to optimize DIM blood and tissue levels during patient transport, imaging and EVT.

Indications and Methods of Use for Parenteral DIM Formulations

DIM Parenteral Premix (2% DIM) is a Neutrophil Inhibitory Agent for the treatment of Acute Ischemic Stroke (AIS) and Acute Coronary Syndrome (ACS).

The dosage form consists of a concentrated sterile premix provided in amber glass single use vials containing 2% Diindolylmethane (DIM) dissolved in sterile excipients. Typical use includes sterile transfer of vial contents into room temperature or warmed 50 cc bags of sterile 0.9% normal saline for injection.

Typical starting dose involves administration of 25-100 mg DIM (12.5-50 cc of saline suspension) over 30 minutes. Starting dose is followed by a controlled rate maintenance dose infusion of 12.5-50 cc per hour to be continued until completion of the EVT and thrombectomy procedure in the case of AIS. In the case of ACS, the same starting and maintenance dose is used before, during, and until completion of coronary artery thrombectomy and the coronary artery stenting procedure.

For preparation of a DIM aqueous dispersion to flush EVT catheters, stent retrievers, and angioplasty devices, the contents of a typical single use 5 cc vial of pre-mix containing 2% Diindolylmethane (DIM) is transferred into 50-100 cc of warm heparinized saline. The suspension is used to flush and clear intravenous and arterial catheters during EVT. Quantities utilized are optionally limited to 25-50 cc of suspension per procedure.

Example 12

Efficacy of DIM to Reduce Neutrophils and NETs in Arterial Thrombosis—Translational Demonstration in an Animal Model Introduction: Prior observations have shown that increased neutrophil and Nuclear Extracellular Trap (NET) content in AIS thrombi contributes to failed thrombolysis (Ducroux et al, supra). In addition, increased NET content in thrombi associates with poor clinical outcome in stroke and myocardial infarction (MI) (Novotny et al. 2020, supra). Together, this human evidence indicates that a therapeutic intervention for AIS and MI which lowers Neutrophil and NET content is clinically relevant. The use of API Diindolylmethane (DIM) administered post thrombosis induction in mice was evaluated in an established model of arterial thrombosis to demonstrate DIM's clinically relevant efficacy as a neutrophil and NET inhibitory agent. The methods employed for induction of carotid and middle cerebral artery thrombosis closely followed an optimized technique which produces consistent thrombosis in groups of animals (Wang X, et al. An optimized murine model of ferric chloride-induced arterial thrombosis for thrombosis research. Thromb Res. 2005; 115(1-2):95-100.). The same model has been used and shows immediate thrombosis formation and obstruction of blood flow within 3 minutes. In addition, accumulation of neutrophils and NETs follows thrombus initiation in mice which is histologically equivalent to the pathologic process in humans (Novotny et al. 2018, Supra). Present inventors employed the same Immunofluorescent (IF) tissue staining of thrombosis specimens and histologic data acquisition techniques as previously described (Novotny et al. 2018, supra) The IF identification of leukocytes was quantified to analyze the modification of the thrombotic process induced by oral and intravenous DIM treatment. DIM was administered using an established Self Micro-Emulsifying Drug Delivery (SMEDD) oral formulation (BR9001, Example 1) and by using a prototype IV formulation (BR2022 IV, Example 4). Administration of DIM after the induction of thromboses emulated the anticipated clinical use of API DIM where therapy will be initiated following the occurrence of AIS and following the onset of symptoms in the Acute Coronary Syndrome (ACS) associated with Acute Myocardial Infarction (AMI).

Materials and Methods:

Animals: All mice were of C57BL6/J background. Specific pathogen-free mice were obtained from Envigo, USA. All mice used for experiments were between 11 and 14 weeks old. Each experimental group was weight and sex-matched so that experiments were carried out on male and female mice with similar weight and in equal sex distribution between groups. All procedures were performed on anaesthetized animals using a uniform technique of inhaled Isoflurane combined with supplemental parenteral agents. Animals were sacrificed under deep anesthesia. All animal experiments were carried out according to the guidelines from the Guide for Care and Use of Laboratory Animals and The Public Health Service (PHS) Policy on Humane Care and Use of Laboratory Animals. All experimental procedures performed on animals met the requirements of the Guide for the protection of animals used for scientific purposes.

Induction of arterial thrombosis after Ferric Chloride exposure: For thrombus induction in the distal carotid artery in vivo, local application of $FeCl_3$ was used following an established method (Wang et al, 2005, supra). In brief, mice were anesthetized using 2-3% inhaled isoflurane, shifting to lower dose maintenance isoflurane and supplemented with a fixed combination of intra-peritoneal buprenorphine, midazolam and dexmedetomidine. The common carotid artery was surgically exposed and bluntly dissected to evenly remove arterial adventitia. Proximal and distal 6.0 sutures were carefully placed without trauma behind the exposed carotid artery. To induce arterial thrombosis, a Gel Blot (GB003) filter paper (1×2 mm), fully saturated with 7.5% $FeCl_3$, was applied for exactly 3 minutes at the upper extreme of the exposed carotid artery. $FeCl_3$ application to the adventitial surface (close to the carotid bifurcation) induced a visible, whitened zone of arterial injury (Wang X et al, supra). To investigate leukocyte accumulation over time, initial thrombus growth was allowed for 10 minutes before residual $FeCl_3$ was removed with irrigation. After visual confirmation of arterial injury at the site of patch application, active and placebo agents were administered as described below. Animals were maintained lightly anesthetized from 4-5 hours to allow thrombosis progression and maturation. Accumulation of leukocytes in both murine and human thrombosis is known to progress over time (Novotny et al. 2018, supra). Warm Lactated Ringers solution was administered intra-peritoneally to mice, maintaining hydration. Body temperature was maintained using a warming blanket system. At the 4-5 hour termination point, sutures were ligated, the thrombus filled carotid artery segment was excised above and below ligated sutures, and the arterial specimen containing the thrombus was fixed in 4% formaldehyde.

Administration of Diindolylmethane Formulations following Thrombosis Initiation: Three Experimental groups were assembled utilizing identical anesthetic and surgical technique: Group 1—oral-gastric Vehicle Excipient Control group, Group 2—Oral-gastric Diindolylmethane based SMEDDS oral formulation (BR9001), and Group 3—IV micellized DIM (BR2022 IV). DIM from oral SMEDDS BR9001 and Vehicle Excipient Control formulations were diluted with sterile water and administered by direct intragastric injection to anesthetized animals in Groups 1 and 2 at 10 minutes following the application of Ferric Chloride patch. Group 3 animals received diluted IV micellized DIM suspension (BR2022 IV) administered intravenously at the same time point following thrombosis initiation. BR9001 delivered intragastric DIM at a DIM dose of 400 mg/kg and was repeated once at 2.5 hours. BR2022 IV delivered intravenous DIM at 40 mg/kg and was repeated once at 2 hours post induction of thrombosis. All agents were first administered at 10 minutes after induction of carotid thrombosis to emulate future clinical use where the first dose of a DIM therapeutic would be initiated after the onset of thrombotic symptoms.

Histologic and Quantitative Evaluation of Carotid Artery Thrombosis Specimens

1. Embedding, sectioning, and Hematoxylin and Eosin (H&E) staining method:

Formalin fixed mouse arterial specimens containing thrombi were transferred to absolute ethanol at 48 hours and submitted for independent laboratory analysis to Premier Laboratory, Longmont, CO. All samples were processed in their entirety to paraffin and embedded distal side down. Serial 4 micron sections were collected, two sections per slide, 38 slides total. Slides 5, 15, 25 and 35 were stained with H&E and scanned at 20× on an Aperio ScanScope AT2. Slide review of H&E slides determined the proximal thrombosis section level with highest leukocyte cellularity. Based on review 2 tissue blocks were further sectioned, stained and examined to assure that the highest cellular portion of each thrombus was uniformly identified. Three, adjacent consecutive sections were advanced to IF staining for quantitative histologic analysis.

2. Immunofluorescent (IF) Staining Methods:

Immunofluorescent (IF) staining was done on the 3 slides with highest cellularity from each of the 16 animals. See the table below for details on primary and secondary antibodies utilized. Slides were baked at 60° C. for 1 hour, deparaffinized in xylene, rinsed in alcohol, and equilibrated in wash buffer (TRIS buffered saline with 0.05% Tween 20; Dako, K8007). Heat induced epitope retrieval (HIER) was performed in a Dako PT Link using a citrate buffer (FLEX TRS Low, pH6; Dako, K8005). Samples were manually stained beginning with application of 3% $H_2O_2$ and serum free protein block (Dako, X0909) for 5 minutes each. Ly6G staining for neutrophils was done using a rat anti-Ly6G (5.0 µg/ml) antibody for 30 minutes, followed by detection with Akoya Opal 520. Slides were then given a microwave heat treatment to strip away any unbound antibodies before additional staining. Slides were cooled and serum free protein block was reapplied. Slides were then stained with a solution of rabbit anti-Histone H3 (5.0 µg/ml) and rat anti-CD45 (0.28 µg/ml) antibodies for 30 minutes. Histone H3 was detected with goat anti rabbit IgG Alexa Fluor 555 plus and CD45 was detected with goat anti rat IgG Alexa Fluor 647 plus. Nuclei were stained with a 5 minute application of DAPI (Invitrogen, D1306). The slides were rinsed in deionized water and coverslipped with Prolong Diamond Antifade Mountant (Invitrogen #P36970).

List of Primary and Secondary Antibodies Used for Immunohistochemistry

| Antigen | Primary Antibody Host | Clone | Provider | Secondary antibody | Provider |
|---------|----------------------|-------|----------|--------------------|----------|
| CD45 | Rat | 30-F11 | R & D Systems, MAB114 | Goat anti-Rat IgG Alexa Fluor 647 Plus | Invitrogen, A48265 |
| Histone H3 | Rabbit | citrulline R2 + R8 + R17 | Abcam, ab5103 | Goat anti-rabbit IgG Alexa Fluor 555 Plus | Invitrogen, A32732 |
| Ly6G | Rat | 1A8 | BD Biosciences, 551459 | Opal 250 | Akoya, FP1487001KT |

3. Image Analysis Methods:

H&E stained slide analysis for Fibrin content: For the H&E stained tissue section with the highest cellularity for each animal, the luminal area within the arterial wall was manually annotated to identify the region for analysis. This annotation also provided the total luminal area in square microns. Percent fibrin area was measured using the Mini-Net Artificial Intelligence (AI) Tissue classification algorithm in Indica Labs HALO software. The algorithm was trained by manually annotating multiple example regions containing histologically distinct Fibrin, and Red Blood Cell (RBC) zones. The algorithm used the color and texture of the tissue within the example regions to identify the histologic structure of each tissue type. Additional training regions were provided until the algorithm was accurately identifying Fibrin, and RBC regions on all images. Percent Fibrin area was calculated by dividing Fibrin area by total luminal area.

Immunofluorecent (IF) stained slide analysis for immune cell subtypes: All IF slides were scanned at 40× using the Vectra 3.0 Multispectral Imaging System. A custom scanning protocol was designed to optimize exposure times for each stain. Prior to analysis the thrombus on each slide was manually annotated for analysis to identify the border of the thrombus at the arterial endothelial margin. This annotation also provides the area of the thrombus in square microns to be extrapolated to 1 $mm^2$ for comparison of specimens.

The HALO's HighPlex FL algorithm was used to measure CD45, and Ly6G positivity. DAPI was identified as the nuclear stain, regions fluorescing in the alexa 647 range were identified as positive for CD45 staining (all leukocytes), and regions fluorescing in the opal 520 range were identified as positive for Ly6G staining (only neutrophils). The algorithm was adjusted to identify weak positive, moderately positive, and strong positive staining using optical density thresholds. Nuclear and cytoplasm detection settings were adjusted as needed until the algorithm was accurately detecting all cells. Among the 3 slides for each animal, the slide showing the highest Leukocyte cellularity was chosen for cell counts and further manual counting of NET structures. NETs were counted by performing a manual cell count using the previously annotated images. NETs were defined as structures overlying or adjacent to Ly6G positive cells that showed positive Cit Histone H3 staining (CitH3 only stains NETs). This included positive Cit Histone H3 staining present as filamentary and cloud-like extracellular structures. The square micrometer (µm) IF cell counting data was extrapolated to cells per square millimeter (mm) for each representative slide. The summary of data was directly submitted from laboratory to independent statistician for analysis.

Statistical Analysis

Data were analyzed using R (RStudio Team (2020). RStudio: Integrated Development for R. RStudio, PBC, Boston, Mass., www.rstudio.com). All cell count data are shown in Results as mean±standard deviation (SD). Initial one-way ANOVAs were performed for each cell type biomarker. Comparisons were made for all possible between-group pairings within each biomarker using two-tailed independent t-tests. A value of $P<0.05$ was considered significant.

Results and Discussion:

The present study results demonstrate that Diindolylmethane (DIM) administered after the onset of arterial thrombosis alters the histologic structure of the developing thrombus resulting in reduced fibrin content and influx of fewer leukocytes and neutrophils. Both intra-gastric and intravenous dosage forms of DIM significantly inhibited the accumulation of prothrombotic neutrophils and NETs in thrombi. Lower levels of neutrophils and NETs in human arterial thrombi are associated with more successful mechanical thrombectomy (Ducroux C, 2018, et al., supra) and better clinical outcome following stroke and myocardial infarction (Novotny J et al, 2020, supra).

Figure 5:
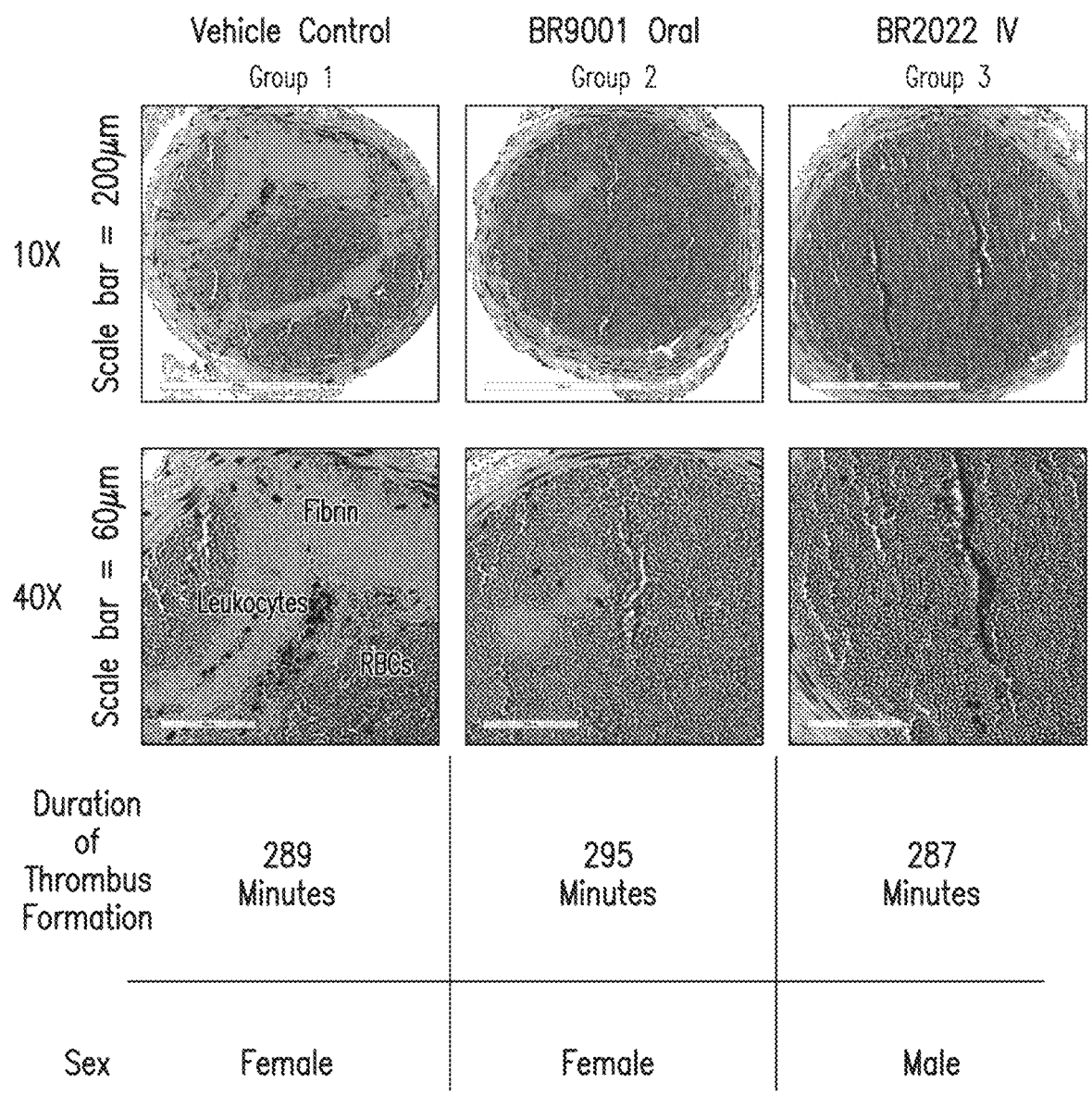
FIG. 5 shows representative images of Hematoxylin & Eosin (H&E) stained tissue sections of carotid artery thromboses, illustrating the comparative composition of thrombi from mice in Group 1 (Vehicle Control), Group 2 (BR9001 Oral, Example 1), and Group 3 (BR2022 IV, Example 4) mice. To allow comparison, the stained appearance of Fibrin, Red Blood Cells (RBCs), and Leukocyte cell components, common to all slides, is identified by overlaid labels in the 40× High Power view of the Vehicle Control animal specimen. The duration of thrombosis formation following initiation with $FeCl_3$ is indicated in minutes. Treatment related changes from DIM were seen in both Female and Male animals.
Figure 6:
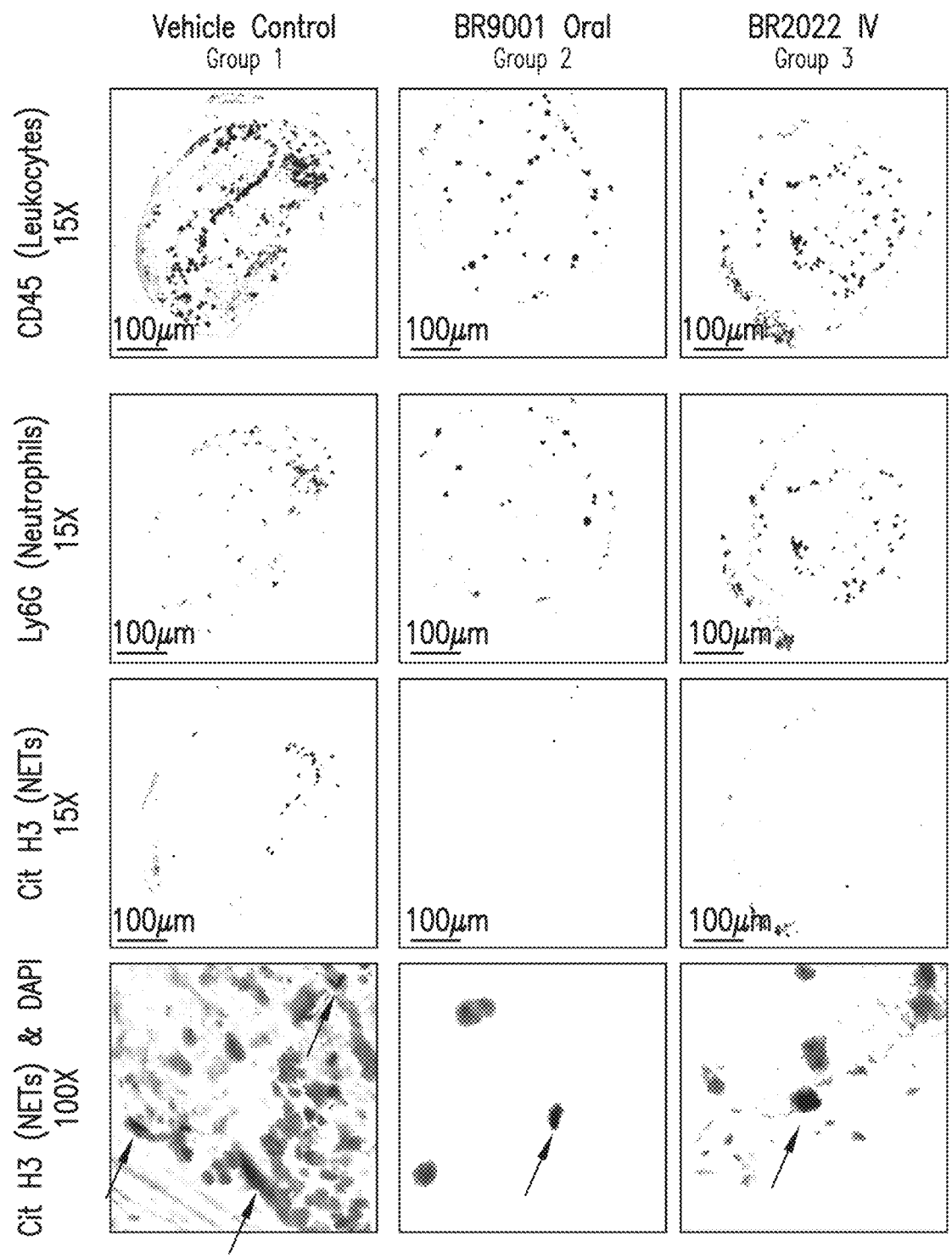
FIG. 6 shows representative images illustrating findings from cell type specific Immunofluorescent (IF) antibody staining of tissue sections of carotid artery thromboses. The images illustrate cellularity in transverse thrombosis sections and are presented with black and white colors inverted for more accurate viewing of cells. Black indicates antibody specific cell staining. The top row of images shows sections stained for all Leukocytes (CD45) found in Group 1, 2 and 3 animals. The second row of images shows sections stained for only Neutrophils (LyG6) found in Groups 1, 2 and 3. The third row of images shows sections stained for only NETs (CitH3) found in Group 1, 2 and 3. The fourth row of images shows High Power portions of row three images chosen to illustrate the presence, frequency and staining characteristics of NETs. Arrows point to filamentous or cloud like NET specific structures.

Vehicle Control (Group 1), BR9001 Oral (Group 2), and BR2022 IV (Group 3) were not different when averaged animal weights, averaged duration of anesthesia, and total minutes from application of Ferric Chloride patch to carotid artery ligation were compared. As demonstrated by H&E staining and histologic evaluation, there is a sharp contrast between Vehicle Control group thrombus composition and the cellular composition of both of the DIM treated groups was appreciated. Control group animals displayed a higher proportion of fibrin and increased presence of leukocytes. In contrast, the DIM treated animals produced less compact thrombi, primarily composed of red cells (RBCs), with a minimum of fibrin and lower presence of leukocytes (See FIG. 5.). The structural stability of thrombi is determined by fibrin content, including density and porosity, with the presence of neutrophils and NETs associated with inflammatory tissue modifications. Thrombi containing predominantly platelets and fibrin are more tightly packed, less compressible, and more adherent to the vessel wall than RBC-rich clots. (Gunning G M, et al. Clot friction variation with fibrin content; implications for resistance to thrombectomy. J Neurointerv. Surg. 2018 January; 10(1):34-38). Such densely packed platelet-fibrin thrombi are also more difficult to extract with mechanical thrombectomy (MT) (Sporns PB. Ischemic Stroke: Histological Thrombus Composition and Pre-Interventional CT Attenuation Are Associated with Intervention Time and Rate of Secondary Embolism. Cerebrovasc Dis. 2017; 44(5-6):344-350).

The image analysis of H&E stained slides using AI acquired data on percent thrombus area occupied by compact Fibrin versus loosely packed RBCs showed a significantly reduced Fibrin percentage in DIM treated animals. Results comparing averaged percentages for animals in Vehicle Control (Group 1), BR9001 Oral (Group 2), and BR2022 IV (Group 3) animals are presented in Table 3.

A significantly reduced Fibrin percentage was found in DIM treated animals compared to Vehicle treated animals. Table 3 presents means and standard deviations for percent Fibrin observed in thrombi of Vehicle Control, BR9001 Oral, BR2022 IV, and combined DIM treatment groups. Initial one-way ANOVA was performed and the resulting p-values were significant (p<0.01), indicating differences among the groups. Follow-on comparisons were made for all possible between-group pairings using two-tailed independent t-tests. Table 3 contains p-values for these comparisons. Compared to Vehicle Control, DIM treatment resulted in a significant reduction in Fibrin percent in thrombi in the BR2022 IV formulation group as well as in the combined Oral and IV DIM treatment groups considered jointly.

TABLE 3

Comparison of Mean Fibrin Percent in Mouse Thrombi by Groups

| Percent Fibrin | Vehicle Control | BR 9001 Oral | BR 2022 IV | All BR |
|---|---|---|---|---|
| Mean (sd) | 51.6 (22.8) | 21.9 (26.3) | 11.0 (5.9) | 16.0 (18.0) |
| | Control v. Oral | Control v. IV | Oral v. IV | Control v. All BR |
| p-Values | 0.092 | 0.002 | 0.346 | 0.004 |

It is expected that other, similar IV DIM formulations, e.g., Formulation #8, Example 11, will provide similar results to that seen with BR2022 IV.

The immunofluorescent (IF) staining methods employed allowed quantification of Leukocytes, Neutrophils, and NETs, identified respectively by labeling with cell specific CD45, LyG6, and CitH3 antibodies. Results from this highly sensitive and quantitative method were in close agreement with the prior results of Novotny et al., 2018 (supra) who utilized the same $FeCl_3$ mouse model to induce thrombosis and the same IF methods for identifying and counting the immune cells within thrombi. Results of the present investigation showed a statistically significant reduction in the presence of leukocytes, neutrophils, and NETs in BR9001 and BR2022 IV treated animals compared to Vehicle Control treated animals. The clear reductions in the presence of leukocytes and the number of neutrophils and NETs accumulated in thrombi of mice are apparent in the representative images from IF staining provided in FIG. 6.

Comparison of cell counts for Leukocytes, Neutrophils, and NETs between Groups 1,2, and 3 using the highest cellularity IF stained section for each thrombosis specimen showed a statistically significant reduction in all cellular components due to DIM treatment. The summarized data, displayed with mean values and SD for cell counts and ranges for each group, are presented in FIG. 7. Statistical analysis reveals a significant treatment effect from DIM administration seen for both the BR9001 oral formulation administered by intra-gastric injection and for the BR2022 IV suspension administered intravenously.

Data from cell counting in IF stained thromboses are presented in Table 4 which contains means (cells/mm$^2$) and standard deviations for Leukocytes, Neutrophils and NETs. Columns compare Vehicle Control (Group 1), BR9001 Oral (Group 2), and BR2022 IV (Group 3) animals. Initial one-way ANOVAs were performed for each biomarker; all p-values were significant (p<0.01), indicating differences among the groups. Follow-on comparisons were made for all possible between-group pairings within each biomarker using two-tailed independent t-tests. Table 5 contains p-values for these comparisons. As can be seen in Table 5, differences were significant between vehicle control and each formulation of DIM for each biomarker. Differences between oral and intravenous formulations of DIM were not significant for any biomarker.

TABLE 4

Means (cells/mm$^2$) and standard deviations for Leukocytes, Neutrophils and NETs in Vehicle Control ,BR9001 Oral and BR2022 IV groups

| Mean Cells/mm$^2$ (sd) | Vehicle Control | BR9001 Oral | BR2022 IV |
|---|---|---|---|
| Leukocytes | 1251.6 (404.7) | 515.2 (415.7) | 661.5 (320.4) |
| Neutrophils | 872.5 (272.3) | 226.8 (175.8) | 461.3 (278.0) |
| NETs | 195.4 (102.3) | 40.4 (36.0) | 46.2 (33.9) |

TABLE 5 p-values for t-tests between each group pair for Leukocytes, Neutrophils and NETs

| p-Values | Control v. Oral | Control v. IV | Oral v. IV |
|---|---|---|---|
| Leukocytes | 0.022 | 0.024 | 0.526 |
| Neutrophils | 0.002 | 0.036 | 0.138 |
| NETs | 0.013 | 0.008 | 0.79 |

It is expected that other, similar IV DIM formulations, e.g., Formulation #8, Example 11, will provide similar results as that seen with BR2022 IV.

The present results demonstrate that DIM treatment significantly reduces the fibrin component of accumulating arterial thromboses. This diminishes the fibrin available for fibrinolysis by tPA and provides a newly described mechanism to reduce release of fibrinolytic products when DIM is administered in combination with the post stroke use of tPA. Prior experimental data demonstrate that tPA coordinately promotes the attraction and extravasation of neutrophils to postischemic tissue via both its proteolytic and nonproteolytic properties (Uhl B, et al. Tissue plasminogen activator promotes postischemic neutrophil recruitment via its proteolytic and nonproteolytic properties. Arterioscler Thromb Vasc Biol. 2014 July; 34(7):1495-504). Combined use of DIM with tPA would be expected to reduce attraction and activation of neutrophils due to tPA activity. Since DIM diminishes both fibrin accumulation in thromboses and in addition directly inhibits neutrophil activation and NETosis, the present results support the combined use of DIM with tPA to reduce tPA driven neutrophil activating activity. Additional evidence shows that neutrophil activation contributes to the clinical occurrence of tPA resistance (Ducroux C, et al., 2018, supra). Combined use of DIM with tPA is proposed to result in improved post stroke reperfusion and outcome from tPA which is currently limited by the neutrophil activating and attraction effects of tPA used alone.

Conclusions: Results of the presents study provide translational evidence of clinically relevant activity for post-AIS administered DIM as a small molecule inhibitor of neutrophil activation and NETosis. The contribution of neutrophils and NETs to the severity and resistance to treatment of arterial thrombosis and associated organ damage in AIS and AMI patients has been confirmed previously. Recent, additional animal models support the present results as on-target for a therapeutic contribution of DIM to MT and AIS since an improved outcome in stroke has been shown to result from depletion of neutrophils (El Amki M, et al. Neutrophils Obstructing Brain Capillaries Are a Major Cause of No-Reflow in Ischemic Stroke. Cell Rep. 2020 Oct. 13; 33(2): 108260.). Based on the present results, suppression of Neutrophil and NET influx using DIM administered after onset of thrombosis in patients can be expected to show therapeutic activity similar to that seen with whole body neutrophil depletion in mice. Suppression of neutrophil activity in AIS is expected to provide clinical benefits in AIS using DIM alone and when DIM is used in conjunction with tPA. The present results showing DIM induced reduction of neutrophils and fibrin in arterial thrombi support clinical use of DIM for the treatment of AIS. With translation into clinical use, DIM's neutrophil inhibitory mechanism of action is appropriate to reduce resistance to the thrombolytic activity of tPA and to improve the clinical outcomes in patients following MT for AIS.

Example 13

Use of Oral and Parenteral DIM Formulations in a Clinically Predictive Model of AIS Introduction:

Further pre-clinical evaluation of oral DIM formulation BR9001 (Example 1) and IV DIM Formulation (Formulation #8, Example 11) will be conducted to demonstrate efficacy endpoints and relevance to meeting unmet needs in treating AIS. To accomplish this, a stroke model in mice is utilized which specifically induces thrombosis of the Middle Cerebral Artery (MCA) and then allows recovery for 24 hours to assess function and histologic evaluation of the stroke lesion. In addition, this model allows evaluation of modification of the influx of Neutrophils and NETs to the brain and stroke penumbra following MCA stoke, as determined by immunofluorescent and other staining of post euthanasia brain tissue. This translational experiment is expected to demonstrate clinically relevant treatment use of oral BR9001 and of parenteral DIM from Formulation #8. Formulation #8 is expected to show similar activity and efficacy to closely related BR2022 IV, which demonstrated efficacy for thrombosis intervention (Example 12). Description of the Materials and Methods to be applied in conducting the translational treatment model follow.

DIM Formulations to be Utilized:

BR9001 Self-Micro-Emulsifying Oral formulation (see Example 1)

Formulation #8 Premix DIM for suspension and parenteral (IV and IP) administration (see Example 11)

Animals and Experimental Model:

All mice will be Swiss albino weighing 21 to 38 g and between 11 and 14 weeks old. Each experimental group will be weight and sex-matched, so experiments are carried out on male and female mice with similar weight and in equal sex distribution between groups. All procedures will be performed on anaesthetized animals using a uniform technique. Animals will be sacrificed under deep anesthesia. All animal experiments will be carried out according to the guidelines from the Guide for Care and Use of Laboratory Animals and The Public Health Service (PHS) Policy on Humane Care and Use of Laboratory Animals. All experimental procedures performed will meet the Guide for the protection of animals used for scientific purposes.

For thrombotic occlusion of the middle cerebral artery (MCA) recapitulating AIS in humans, the ferric chloride ($FeCl_3$) stroke model will be performed. Briefly, the scalp and skull will be opened, and the MCA will be visualized with the with a stereomicroscope, $FeCl_3$ (20%) will be placed over the intact duramater on the artery for 10-29 minutes, as described previously (Karatas H, et al. Thrombotic distal middle cerebral artery occlusion produced by topical FeCl(3) application: a novel model suitable for intravital microscopy and thrombolysis studies. J Cereb Blood Flow Metab 2011; 31:1452-1460). After surgery mice will be allowed to emerge from anesthesia. Study formulations will be administered as described below. Animals will then be returned to their home cages to recover for 24 hours.

Experimental Groups:
1. Sham Control—Gavage administration of water—surgery without craniotomy.
2. Vehicle Control—Gavage administration of water. Craniotomy with AIS equivalent MCA thrombosis.
3. Oral Treatment Group—Gavage administration of BR9001 (Example 1) dispersed in water. Craniotomy with AIS equivalent MCA thrombosis.
4. Parenteral Treatment Group—DIM IV Formulation #8 (Example 11). Craniotomy with AIS equivalent MCA thrombosis.

Evaluation of Neurological Deficits:

At 24 hours post emergence, neurologic deficits will be measured by established methods for mice (Hernandez-Jimenez M et al. Test repositioning for functional assessment of neurological outcome after experimental stroke in mice. PLoS One. 2017; 12:e0176770). Motor score will be derived from spontaneous activity, symmetry of limb movements, climbing, balance and coordination. Sensory score will be derived from body proprioception, vibrissae, and tactile responses.

Brain Histology Evaluation, and Quantification of Neutrophils and NETs in Brain Tissue Following euthanasia, mice will be perfused intracardially. The brains will be removed intact and fixed with formaldehyde. For histochemical and immunofluorescent histology, brains will be postfixed with paraformaldehyde, cryoprotected in 30% sucrose and frozen. Subsequently, 5 and/or 15 µm-thick sections will be obtained in the cryostat. For immunofluorescent staining, sections will be first incubated with blocking solution (BSA 0.5%, normal serum 10% and Triton X-100 0.25% in PBS); next, primary antibodies will be incubated overnight. Primary antibodies to be utilized include CitHE and Ly6G using methods as described in Example 12. Using a microscope, NETs will be identified by immunofluorescence analysis. H&E staining and other penumbra specific staining will be performed on additional, representative brain sections and examined by light microscopy.

Expected Results and Significance:

Expected results from this translational treatment model for AIS in humans include improved functional outcomes in DIM treated Groups compared to the Vehicle Control group. Using this MS model, the formation and composition of induced thromboses in mice is known to be histologically similar to arterial thromboses in humans (Novotny et al., 2018, supra). The present AIS model, involving the MCA, duplicates the anatomic location, thrombotic occlusion, and resulting ischemic stroke seen in AIS patients. This experiment is expected to provide preclinical evidence of efficacy for analogous clinical intervention using oral BR9001 and intravenous micellized DIM from Formulation #8 (see Example 11). Such pre-clinical evidence will support early-stage clinical trials for the therapeutic use of DIM formulations in patients suffering from AIS. This includes AIS patients treated with and without co-administered tPA, and in patients undergoing MT for AIS.

This disclosure is not to be limited in scope by the embodiments disclosed in the examples which are intended as single illustrations of individual aspects, and any equivalents are within the scope of this disclosure. Various modifications in addition to those shown and described herein will become apparent to those skilled in the art from the foregoing description. Such modifications are intended to fall within the scope of the appended claims.

Various references such as patents, patent applications, and publications are cited herein, the disclosures of which are hereby incorporated by reference herein in their entireties.

What is claimed is:

1. A composition, comprising about 2 wt % DIM, about 45 wt % anhydrous ethanol, about 10 wt % medium chain triglycerides of caprylic (C8) and capric (C10) acids, about 8 wt % phosphatidyl choline, about 15 wt % polyoxyl 15 hydroxystearate, about 8 wt % of poloxamer 188, and about 12 wt % of poloxamer 407.

2. The composition of claim 1, further comprising all trans retinoic acid.

3. A pharmaceutical composition, comprising the composition of claim 1 and sterile 0.9% normal saline for injection.

4. A pharmaceutical composition, comprising the composition of claim 1 and sterile 0.9% normal saline for injection, wherein the ratio of the composition of claim 1 to the sterile 0.9% normal saline for injection is about 1:10.

5. A pharmaceutical composition, comprising 5 g of the composition of claim 1 and 50 cc of sterile 0.9% normal saline for injection.

* * * * *